(12) United States Patent
Beavers et al.

(10) Patent No.: US 7,696,234 B2
(45) Date of Patent: *Apr. 13, 2010

(54) HISTAMINE H3 RECEPTOR AGENTS, PREPARATION AND THERAPEUTIC USES

(75) Inventors: Lisa Selsam Beavers, Franklin, IN (US); Robert Alan Gadski, Indianapolis, IN (US); Cynthia Darshini Jesudason, Indianapolis, IN (US); Richard Todd Pickard, Noblesville, IN (US); Freddie Craig Stevens, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 576 days.

This patent is subject to a terminal disclaimer.

(21) Appl. No.: 11/569,803

(22) PCT Filed: May 24, 2005

(86) PCT No.: PCT/US2005/018249

§ 371 (c)(1),
(2), (4) Date: Nov. 30, 2006

(87) PCT Pub. No.: WO2005/121080

PCT Pub. Date: Dec. 22, 2005

(65) Prior Publication Data

US 2009/0118254 A1    May 7, 2009

Related U.S. Application Data

(60) Provisional application No. 60/576,421, filed on Jun. 2, 2004.

(51) Int. Cl.
*A61K 31/4439*  (2006.01)
*A61K 31/4025*  (2006.01)
*C07D 401/14*   (2006.01)
*C07D 207/04*   (2006.01)
*C07D 205/04*   (2006.01)

(52) U.S. Cl. .................. 514/343; 514/422; 546/276.4; 548/518; 548/950

(58) Field of Classification Search ............... 514/343, 514/422; 546/276.4; 548/518, 950
See application file for complete search history.

(56) References Cited

FOREIGN PATENT DOCUMENTS

| EP | 0 197 840 | 10/1986 |
|---|---|---|
| EP | 0 238 319 | 9/1987 |
| EP | 0494 010 | 7/1992 |
| WO | WO 96/38141 | 12/1996 |
| WO | WO 96/38142 | 12/1996 |
| WO | WO 00/12507 | 3/2000 |
| WO | WO 02/076925 | 10/2002 |
| WO | WO 03/064411 | 8/2003 |
| WO | WO 2004/024715 | 3/2004 |

OTHER PUBLICATIONS

"Parkinson's Disease." Retrieved online via Internet [Apr. 6, 2009], URL: www.nlm.nih.gov/medlineplus/parkinsonsdisease.html.*

* cited by examiner

*Primary Examiner*—Kamal A Saeed
*Assistant Examiner*—Samantha L Shterengarts
(74) *Attorney, Agent, or Firm*—Dan L. Wood

(57) ABSTRACT

The present invention discloses novel compounds of Formula I or pharmaceutically acceptable salts thereof which have histamine-H3 receptor antagonist or inverse agonist activity, as well as methods for preparing such compounds. In another embodiment, the invention discloses pharmaceutical compositions comprising compounds of Formula I as well as methods of using these compositions to treat obesity, cognitive deficiencies, narcolepsy, and other histamine H3 receptor-related diseases.

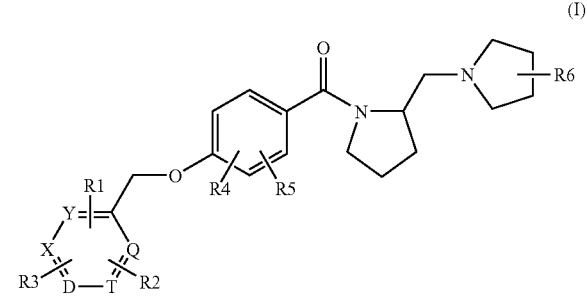

13 Claims, No Drawings

HISTAMINE H3 RECEPTOR AGENTS, PREPARATION AND THERAPEUTIC USES

This is the national phase application, under 35 U.S.C. 371, for PCT International Application No. PCT/US2005/018249 filed 24 May, 2005, which claims the benefit under 35 U.S.C. 119(e) to U.S. Provisional Application No. 60/576,421 filed 2 Jun., 2004.

The present invention relates to novel benzyl ether compounds, as well as intermediates and methods for preparing such compounds, and to the use of these compounds as pharmaceutical compositions, and to pharmaceutical compositions comprising the compounds, and to methods of treatment employing these compounds and compositions.

Histaminergic neurons originate in the tuberomammilary region of the hypothalamus and project to practically all areas of the brain. The histamine H3 receptor (H3R) is relatively neuron specific and inhibits the release of a number of monoamines, including histamine. The histamine H3 receptor is a presynaptic autoreceptor, and hetero-receptor, located both in the central and the peripheral nervous system. Histamine H3 receptors are autoreceptors modulating histamine release, or heteroreceptors modulating the cellular release of other neurotransmitters, including dopamine, serotonin, and acetylcholine. These are examples of H3 receptor mediated cellular responses.

Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-regulated neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists, and antagonists could be important mediators of neuronal activity, and the activities of other cells that may express this receptor.

Inverse agonism or selective antagonism of the histamine H3 receptor raises brain levels of histamine, and other monoamines, and inhibits activities such as food consumption while minimizing non-specific peripheral consequences. By this mechanism, they induce a prolonged wakefulness, improved cognitive function, reduction in food intake and normalization of vestibular reflexes. Accordingly, the histamine H3 receptor is an important target for new therapeutics in Alzheimer disease, mood and attention adjustments, cognitive deficiencies, obesity, dizziness, schizophrenia, epilepsy, sleeping disorders, narcolepsy and motion sickness.

Histamine mediates its activity via four receptor subtypes, H1R, H2R, H3R and a newly identified receptor designated GPRv53 [(Oda T., et al., J. Biol. Chem. 275 (47): 36781-6 (2000)]. Alternative names for the GPRv53 receptor are PORT3 or H4R. Although relatively selective ligands have been developed for H1R, H2R and H3R, few specific ligands have been developed that can distinguish H3R from H4R. H4R is a widely distributed receptor found at high levels in human leukocytes. Activation or inhibition of this receptor could result in undesirable side effects when targeting antagonism of the H3R receptor. The identification of the H4R receptor has fundamentally changed histamine biology and must be considered in the development of histamine H3 receptor antagonists.

Some histamine H3 receptor antagonists were created which resembled histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO96/38142. These imidazole-containing compounds have the disadvantage of poor blood-brain barrier penetration, interaction with cytochrome P-450 proteins, and hepatic and ocular toxicities. Recently other imidazole and non-imidazole ligands of the histamine H3 receptor have been described. The compounds of the present invention differ in structure from the compounds described in the art.

There remains a need for improved treatments using alternative or improved pharmaceutical agents that act as histamine H3 receptor agonists, inverse agonists, or antagonists, to modulate H3 receptor activity, and treat the diseases that could benefit from H3 receptor modulation. The present invention provides such a contribution to the art based on the finding that a novel class of benzyl ether compounds have high affinity, selective, and potent activity at the histamine H3 receptor. The subject invention is distinct in the particular structures and their activities.

SUMMARY OF THE INVENTION

The present invention provides a compound structurally represented by Formula I:

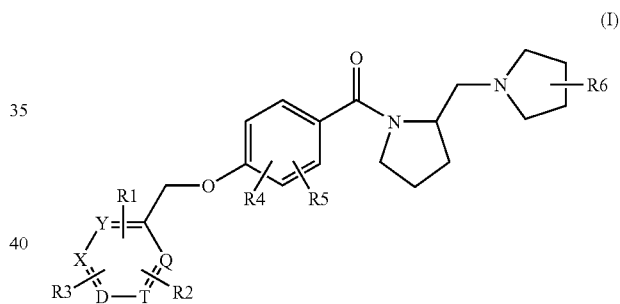

or a pharmaceutically acceptable salt thereof wherein:

Q, T, D, X, and Y independently represent carbon (substituted with hydrogen or the optional substituents indicated herein) or nitrogen, provided that no more than two of Q, T, D, X, and Y are nitrogen;

R1, R2, and R3 are independently at each occurrence
—H, -halogen, —($C_1$-$C_7$)alkyl (optionally substituted with one to three halogens), —$CF_3$, —CN, —C(O)R10, —CO(O)R7, —CO(O)Li, —C(O)($C_3$-$C_5$)cycloalkyl, —C(O)NR7R8, —$OCF_3$, —OR7, —NR7R8, —NR9$SO_2$R7, —NR9C(O)R7, —NR9$CO_2$R7, —NR9C(O)NR7R8, —SR7, —$SO_2$R7, —$SO_2CF_3$, —$SO_2$ NR7R8, —S(O)R7, —$CH_2SO_2$R10, or -heteroaryl-R9;

provided however that wherein D is nitrogen, then R1 or R2 or R3 are not attached to D, and provided that when X is nitrogen, then R1 or R2 or R3 are not attached to X, and provided that when T is nitrogen, then R1 or R2 or R3 are not attached to T, and provided that when Q is nitrogen, then R1 or R2 or R3 are not attached to Q; and provided that when Y is nitrogen, then R1 or R2 or R3 are not attached to Y;

R4 and R5 are independently at each occurrence
—H, —OH, -halogen, —CF$_2$H, —CF$_3$, —(C$_1$-C$_3$)alkyl (optionally substituted with one to three halogens), or —OR9;

R6 is
—H, -halogen, —CF$_3$, —(C$_1$-C$_3$)alkyl (optionally substituted with one to three halogens), —NH$_2$, —NR7R8, —OH, or —OR7;

R7 and R8 are independently at each occurrence
—H or —(C$_1$-C$_7$)alkyl (optionally substituted with one to three halogens), wherein R7 and R8 can combine with the atom to which they are attached to form a three to seven membered ring;

R9 is —H or —(C$_1$-C$_3$)alkyl (optionally substituted with one to three halogens); and R10 is —H, —(C$_1$-C$_7$)alkyl (optionally substituted with one to three halogens), or -phenyl.

The present invention provides compounds of Formula I which show a selective and high affinity binding for the histamine H3 receptor, and thus are useful as histamine H3 receptor antagonists or inverse agonists. The present invention further provides an antagonist or inverse agonist of Formula I which is characterized by having greater affinity for the histamine H3 receptor as compared to the affinity for the H4R receptor. In another aspect the invention provides intermediates and methods for making the compounds of Formula I. In yet another aspect, the present invention provides a pharmaceutical composition which comprises a compound of Formula I, or a pharmaceutically acceptable salt thereof, and a pharmaceutically acceptable carrier, diluent, or excipient. In addition, the present invention provides a methods for the treatment of nervous system disorders, and other disorders associated with histamine H3 receptor, comprising administering to a patient in need thereof an effective amount of a compound of Formula I or a pharmaceutical composition of Formula I.

DETAILED DESCRIPTION OF THE INVENTION

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R.

The term "H3R" means the histamine H3 receptor that inhibits the release of a number of monoamines, including histamine.

The term "H1R" means the histamine H1 receptor subtype.

The term "H2R" means the histamine H2 receptor subtype.

The term "H3R antagonists" is defined as a compound of the present invention with the ability to block forskolin-stimulated cAMP production in response to agonist R (−)α methylhistamine. The term "H3R inverse agonist" is defined as a compound of the present invention with the ability to inhibit the constitutive activity of H3R. "Selective H3R antagonists or inverse agonists" means a compound of the present invention having a greater affinity for H3 histamine receptor than for H4R histamine receptor.

In the general formulae of the present document, the general chemical terms have their usual meanings. For example;

"(C$_1$-C$_3$)alkyl" are one to three carbon atoms such as methyl, ethyl, propyl, and the like, optionally substituted with one to three halogens, and "(C$_1$-C$_7$)alkyl" are one to seven carbon atoms such as methyl, ethyl, propyl, butyl, pentyl, hexyl, heptyl, and the like, and branched or isomeric forms thereof, optionally substituted with one to three halogens.

"(C$_3$-C$_5$)Cycloalkyl" means a ring with three to seven carbon atoms such as cyclopropyl, cyclobutyl, cyclopentyl and cyclohexyl, cycloheptyl, and the like.

"Heteroaryl" means a monocyclic aromatic ring containing five atoms, and containing at least one ring heteroatom selected from N, O and S (including SO and SO$_2$). Examples of heteroaryl include pyrrolyl, isoxazolyl, isothiazolyl, pyrazolyl, oxazolyl, oxadiazolyl, thiadiazolyl, thiazolyl, imidazolyl, triazolyl, tetrazolyl, furanyl, thienyl, and the like.

"Boc" or "BOC" refer to t-butyl carbamate. "HOBt" is 1-hydrobenzotriazole. "PS-Trisamine" is Tris-(2-aminoethyl)amine polystyrene. "PS-Carbodiimide" or "PS-CDI" is N-Cyclohexylcarbodiimide-N'-propyloxymethyl polystyrene. "PS-DIEA" is N,N-(Diisopropyl)aminomethylpolystyrene (1% inorganic antistatic agent). "PS-DMAP" is N-(methylpolystyrene)-4-(methylamino) pyridine.

"Halogen" or "halo" means fluoro, chloro, bromo and iodo.

The term "optionally substituted" as used herein means that the groups in question are either unsubstituted or substituted with one or more of the substituents specified. When the groups in question are substituted with more than one substituent the substituents may be the same or different.

Furthermore, when using the terms "independently,". "independently are," and "independently selected from," it should be understood that the groups in question may be the same or different.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s) including compound(s) of Formula I and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

Certain of the above defined terms may occur more than once in the structural formulae, and upon such occurrence each term shall be defined independently of the other.

In one embodiment, the present invention provides compounds of Formula I as described in detail above. While all of the compounds of the present invention are useful, certain of the compounds are particularly interesting and are preferred. The following listing sets out several groups of preferred compounds. It will be understood that each of the listings may be combined with other listings to create additional groups of preferred embodiments. Other embodiments are, 1. wherein Q, T, D, X, and Y are carbon (substituted with hydrogen or the optional substituents indicated herein),
2. wherein X is carbon and R1 is attached to X,
3. wherein D is carbon and R1 is attached to D,
4. wherein Y is carbon and R1 is attached to Y,
5. wherein D is carbon and R1 is attached to D and R1 is selected from the group consisting of $-NR9SO_2R7$, $-SO_2R7$, $-SO_2CF_3$, $-SO_2NR7R8$, and $-S(O)R7$,
6. wherein R2 is halogen,
7. wherein one of Q, T, D, X, or Y is nitrogen,
8. wherein Q is nitrogen,
9. wherein T is nitrogen,
10. wherein D is nitrogen,
11. wherein X is nitrogen,
12. wherein Y is nitrogen,
13. wherein two of Q, T, D, X, or Y are nitrogen,
14. wherein D and Q are nitrogen,
15. wherein T and X are nitrogen,
16. wherein D and Y are nitrogen,
17. wherein D and Q are nitrogen,
18. wherein Q and Y are nitrogen,
19. wherein R4 is halogen,
20. wherein R4 is halogen and R5 is halogen,
21. wherein R6 is $-(C_1-C_3)$ alkyl (optionally substituted with one to three halogens),
22. wherein R6 is $CH_3$,
23. wherein R1 is -halogen, $-(C_1-C_7)$ alkyl (optionally substituted with one to three halogens), $-CN$, $-C(O)$ R10, $-CO(O)Li$, $-C(O)(C_3-C_5)$cycloalkyl, $-C(O)$ $NR7R8$, $-OCF_3$, $-OR7$, $-NR7R8$, $-NR9SO_2R7$, $-NR9C(O)R7$, $-NR9CO_2R7$, $-NR9C(O)NR7R8$, $-SR7$, $-SO_2R7$, $-SO_2CF_3$, $-SO_2 NR7R8$, $-S(O)$ R7, $-CH_2 SO_2NR10$, or heteroaryl-R9, and R2 and R3 are independently at each occurrence $-H$, -halogen, $-(C_1-C_7)$ alkyl (optionally substituted with one to three halogens), $-CN$, $-C(O)R7$, $-C(O)(C_3-C_5)$cycloalkyl, $-C(O)NR7R8$, $-OCF_3$, $-OR7$, $-NR7R8$, $-NR9SO_2R7$, $-NR9C(O)R7$, $-NR9CO_2R7$, $-NR9C(O)NR7R8$, $-SR7$, $-SO_2R7$, $-SO_2CF_3$, $-SO_2 NR7R8$, $-S(O)R7$, $-CH_2SO_2NR10$, or heteroaryl-R9, and R4 and R5 are independently $-H$, $-OH$, -halogen, $-CF_2H$, $-CF_3$, $-(C_1-C_3)$alkyl (optionally substituted with one to three halogens), or $-OR9$, provided that when R4 is $-H$, then R5 is not $-H$.

Due to their interaction with the histamine H3 receptor, the compounds and compositions of the present invention are useful in the treatment of a wide range of conditions and disorders in which an interaction with the histamine H3 receptor is beneficial. Thus, the compounds may find use for example to prevent, treat, and/or alleviate diseases or conditions of the central nervous system, the peripheral nervous system, the cardiovascular system, the pulmonary system, the gastrointestinal system and the endocrinological system, while reducing and or eliminating one or more of the unwanted side effects associated with the current treatments. Such diseases or conditions include those responsive to the modulation of histamine H3 receptors, such as nervous system disorders. These disorders are referred to herein as "nervous system disorders and other disorders associated with histamine H3 receptor". "Nervous system disorders and other disorders associated with histamine H3' receptor" include, but are not limited to, diseases or conditions such as obesity, cognitive disorders, attention deficit disorders, memory processes, dementia, cognition disorders, Alzheimer's disease, attention-deficit hyperactivity disorder, bipolar disorder, cognitive deficits, mild cognitive impairment, cognitive deficits in psychiatric disorders, deficits of memory, deficits of learning, migraine, mood alteration, attention alteration, motion sickness, narcolepsy, neurogenic inflammation, obsessive compulsive disorder, Parkinson's disease, schizophrenia, depression, epilepsy, seizures or convulsions; sleep disorders such as narcolepsy; vestibular dysfunction such as Meniere's disease; pain, drug abuse, jet lag, impaired wakefulness, Tourette's syndrome, vertigo, and the like; as well as cardiovascular disorders such as acute myocardial infarction; cancer such as cutaneous carcinoma, medullary thyroid carcinoma and melanoma; respiratory disorders such as asthma; gastrointestinal disorders, inflammation, and septic shock, diabetes, type II diabetes, insulin resistance syndrome, metabolic syndrome, polycystic ovary syndrome, Syndrome X, and the like. The methods of this invention encompass a prophylactic or therapeutic administration of a compound of Formula I.

In addition, the present invention provides a compound of Formula I, or a pharmaceutical salt thereof, or a pharmaceutical composition of Formula I, for use in inhibiting the histamine H3 receptor; for use in inhibiting a histamine H3 receptor mediated cellular response in a mammal; for use in selectively increasing histamine levels in cells or increasing histamine release by cells; for use in treating a disease arising from excessive histamine H3 receptor activity; for use in treating nervous system disorders and other disorders associated with histamine H3 receptor in a mammal; and for use in treating memory process deficiencies, dementia, cognitive disorders, Alzheimer's disease, attention-deficit hyperactivity disorder, Parkinson's disease, schizophrenia, depression, epilepsy, seizures or convulsions, sleep disorders, fatigue, alertness deficits, vestibular dysfunction, migraine, motion sickness, obesity, and pain.

The present invention is further provides the use of a compound of Formula I, or a pharmaceutical salt thereof, or a pharmaceutical composition of Formula I, for the manufacture of a medicament for inhibiting the histamine H3 receptor; for the manufacture of a medicament for inhibiting a histamine H3 receptor mediated cellular response in a mammal; for the manufacture of a medicament for selectively increasing histamine levels in cells, or increasing histamine release by cells; for the manufacture of a medicament for treating a disease arising from excessive histamine H3 receptor activity; for the manufacture of a medicament for treating nervous system disorders and other disorders associated with histamine H3 receptor in a mammal; and for the manufacture of a medicament for treating memory process deficiencies, dementia, cognitive disorders, Alzheimer's disease, attention-deficit hyperactivity disorder, Parkinson's disease, schizophrenia, depression, epilepsy, seizures or convulsions, sleep disorders, fatigue, alertness deficits, vestibular dysfunction, migraine, motion sickness, obesity, and pain.

The present invention further provides a method of treating conditions resulting from excessive histamine H3 in a mammal; a method of inhibiting the histamine H3 receptor in a mammal; a method of inhibiting a histamine H3 receptor mediated cellular response in a mammal; a method of selectively increasing histamine levels in cells, or increasing histamine release by cells in a mammal; a method of treating nervous system disorders and other disorders associated with histamine H3 receptor in a mammal; and a method of treating memory process deficiencies, dementia, cognitive disorders, Alzheimer's disease, attention-deficit hyperactivity disorder, Parkinson's disease, schizophrenia, depression, epilepsy, seizures or convulsions, sleep disorders, fatigue, alertness deficits, vestibular dysfunction, migraine, motion sickness, obesity, and pain; comprising administering to a mammal in need of such treatment a histamine H3 receptor-inhibiting amount of a compound of Formula I or a pharmaceutically acceptable salt thereof, or a pharmaceutical composition of Formula I.

In addition, the present invention provides a pharmaceutical composition of Formula I adapted for use in inhibiting the histamine H3 receptor; adapted for use in inhibiting histamine H3 receptor mediated cellular responses; adapted for use in selectively increasing histamine levels in cells, or increasing histamine release by cells; adapted for use in treating nervous system disorders and other disorders associated with histamine H3 receptor in a mammal; and adapted for use in preventing for treating memory process deficiencies, dementia, cognitive disorders, Alzheimer's disease, attention-deficit hyperactivity disorder, Parkinson's disease, schizophrenia, depression, epilepsy, seizures or convulsions, sleep disorders, fatigue, alertness deficits, vestibular dysfunction, migraine, motion sickness, obesity, and pain.

Furthermore, compounds of the present invention may be applicable as diagnostic agents for identifying patients having a defect in the histamine H3 receptor. Embodiments of the invention include the examples described herein, synthesized by methods described herein and supplemented by methods in the art, as positron emitting tomography (PET) ligands. In another embodiment the intermediate compounds are useful for preparing final compounds of the invention, or may themselves possess H3 antagonist or inverse agonist activity.

As used herein, the term "stereoisomer" refers to a compound made up of the same atoms bonded by the same bonds but having different three-dimensional structures. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The compounds of the present invention may be chiral, and it is intended that any enantiomers, as separated, pure, or partially purified enantiomers, or racemic mixtures thereof, are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure, or partially purified diastereomers, or mixtures thereof are included within the scope of the invention. Furthermore, some of the compounds of the present invention may exist in different tautomeric forms and it is intended that any tautomeric forms which the compounds are able to form are included within the scope of the present invention. Thus, as one skilled in the art knows, certain aryls may exist in tautomeric forms. The invention also includes tautomers, enantiomers and other stereoisomers of the compounds of Formula I. Such variations are contemplated to be within the scope of the invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation "━━" refers to a bond that protrudes forward out of the plane of the page. The designation "┈┈┉" refers to a bond that protrudes backward out of the plane of the page. The designation "∿∿" refers to a bond wherein the stereochemistry is not defined.

The compounds of Formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen," *Stereochemistry of Organic Compounds*," (Wiley-Interscience 1994), and European Patent Application No. EP-A-838448, published Apr. 29, 1998. Examples of resolutions include recrystallization techniques or chiral chromatography.

In general, the term "pharmaceutical" when used as an adjective means substantially non-toxic to living organisms. For example, the term "pharmaceutical salt" as used herein, refers to salts of the compounds of Formula I which are substantially non-toxic to living organisms. See, e.g., Berge, S. M, Bighley, L. D., and Monkhouse, D. C., "Pharmaceutical Salts," *J. Pharm. Sci.,* 66:1, 1977. The present invention also encompasses pharmaceutically acceptable salts of the present compounds. Such salts include pharmaceutically acceptable acid addition salts, pharmaceutically acceptable metal salts, ammonium and alkylated ammonium salts. Also intended as pharmaceutically acceptable acid addition salts are any hydrates that the present compounds are able to form. Furthermore, the pharmaceutically acceptable salts comprise basic amino acid salts such as lysine, arginine and ornithine. Typical pharmaceutical salts include those salts prepared by reaction of the compounds of Formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I prepared by reaction of a compound of Formula I with a mineral or organic acid. For exemplification of pharmaceutical acid addition salts see, e.g., Berge, S. M, Bighley, L. D., and Monkhouse, D. C., *J. Pharm. Sci.,* 66:1, 1977. Since compounds of this invention may be basic in nature, they accordingly react with any of a number of inorganic and organic acids to form pharmaceutical acid addition salts.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, ethanesulfonic acid, methanesulfonic acid, oxalic acid, p-bromophenylsulfonic acid, carbonic acid, succinic acid, citric acid, tartaric acid, benzoic acid, acetic acid and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The skilled artisan would appreciate that some compounds of Formula I may be acidic in nature and accordingly react with any of a number of inorganic and organic bases to form pharmaceutical base addition salts. The term "base addition salt" refers to a salt of a compound of Formula I prepared by reaction of a compound of Formula I with a mineral or organic base. For exemplification of pharmaceutical base addition salts see, e.g., Berge, S. M, Bighley, L. D., and Monkhouse, D. C., *J. Pharm. Sci.,* 66:1, 1977. Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I. The potassium and sodium salt forms are particularly preferred. The present invention also contemplates pharmaceutical base addition salts of compounds of Formula I.

The pharmaceutical salts of the invention are typically formed by reacting a compound of Formula I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

All pharmaceutically acceptable salts of the compounds of Formula I are contemplated in the scope of the present invention. The compounds of the present invention may form solvates with low molecular weight solvents. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into a compound of the present invention. Conventional procedures for the selection and preparation of suitable prodrug derivatives are described, for example in "Design of Prodrugs", ed. H. Bundgaard, Elsevier, 1985.

The compounds of Formula I can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Procedures, Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates (M+1) unless indicated otherwise. "MS(FD)" refers to field desorption mass spectrometry, "MS(IS)" refers to ion spray mass spectrometry, "MS(FIA)" refers to flow injection analysis mass spectrometry, "MS(FAB)" refers to fast atom bombardment mass spectrometry, "MS(EI)" refers to electron impact mass spectrometry, "MS(ES)" refers to electron spray mass spectrometry, "UV" refers to ultraviolet spectrometry, "$^1$H NMR" refers to proton nuclear magnetic resonance spectrometry. In addition, "IR" refers to infrared spectrometry, and the absorption maxima listed for the IR spectra are only those of interest and not all of the maxima observed. "RT" refers to room temperature.

General Preparations:

SCHEME A

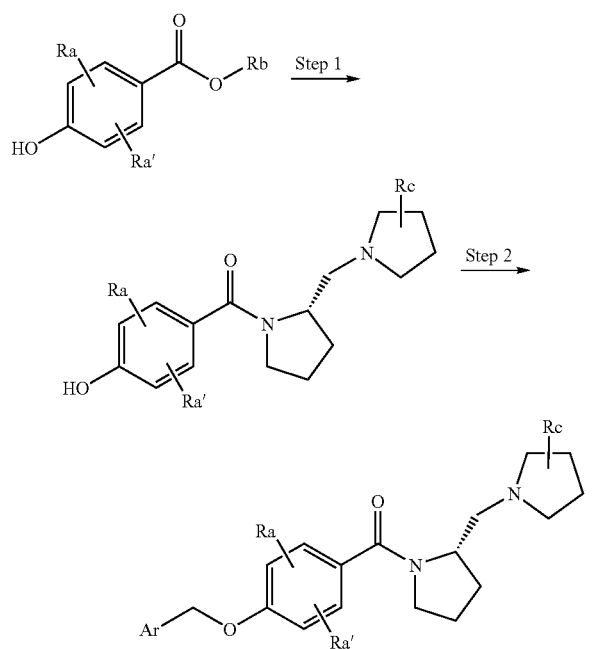

In Scheme A, $R_a$ and $R_{a'}$ are each independently but not limited to F, Cl, $CF_3$, alkyl and can include disubstituted compounds; $R_b$ is H, or the corresponding carboxylic acids salts; $R_c$ can be but is not limited to alkyl, amino, hydroxy, and Ar is any mono, di or trisubstituted six-membered aromatic or heteroaromatic ring not limited to phenyl, pyridine, pyrimidine, pyrazine, pyridazine. In Scheme A, Step 1 aryl carboxylic acids or the lithium, sodium or potassium salt of the acid where $R_b$ can be H, Li, Na or K are converted to the corresponding amides using a number of different methods known in the literature. Some of these methods can be found described in a review of coupling reagents in peptide synthesis by Klausner & Bodarisky, Synthesis, 1972, 9, 453-463.

For example, 4-hydroxybenzoic acid or the corresponding lithium or sodium salt is suspended a suitable organic solvent such as dichloromethane, DMF or mixtures thereof. A suitable amide coupling agent i.e EDC, DCC, TBTU, etc., is added followed by HOBt, HATU, etc., at room temperature. Diisopropylethyl amine and suitable amine in this case, (S) (+)-1-(2-pyrrolidinylmethyl)pyrrolidine are added to the mixture. The mixture is stirred at room temperature for a period of 8-48 hours. The reaction is quenched by addition of water. The resulting mixture may be extracted, concentrated and purified according to techniques well known in the art.

Alternatively the corresponding acid chloride can be formed from the corresponding acid or salt thereof using thionyl chloride or oxalyl chloride and a few drops DMF, and treated with a suitable amine to give the desired amide.

In Scheme A, Step 2 the phenols are converted to the benzyl ethers by alkylation with alkyl bromides, chlorides, iodides, mesylates, tosylate etc. with a suitable base such as $Cs_2CO_3$, $K_2CO_3$, or triethylamine etc. in a suitable solvent such as DMF, acetone, THF or $CH_2Cl_2$. The alkylation can carried out at room temperature or with heating.

For example, (4-Hydroxy-phenyl)-(2-(S)-pyrrolidin-1-ylmethyl-pyrrolidin-1-yl)-methanone where Ra, Ra'=H and $Cs_2CO_3$ are suspended in DMF and 3-(bromomethyl)pyridine hydrobromide is added. The mixture is stirred at room temperature for 24-48 h. After an aqueous workup, the crude material may be purified by well known techniques.

Alternatively the benzyl ether can be formed by a Mitsunobu or related reaction using an alkyl alcohol and a coupling agent such as DEAD, DIAD, etc., with triphenyl phosphine in a suitable solvent such as THF or $CH_2Cl_2$. The reaction is quenched with water, and the resulting mixture may be extracted, concentrated, and purified according to techniques well known in the art.

For example, DEAD is added to a mixture of (4-Hydroxy-phenyl)-(2-(S)-pyrrolidin-1-ylmethyl-pyrrolidin-1-yl)-methanone, pyrazin-2-yl-methanol, and triphenylphosphine, in a suitable solvent such as THF. The mixture is stirred at room temperature overnight. The resulting mixture may be extracted, concentrated and purified according to techniques well known in the art.

SCHEME B

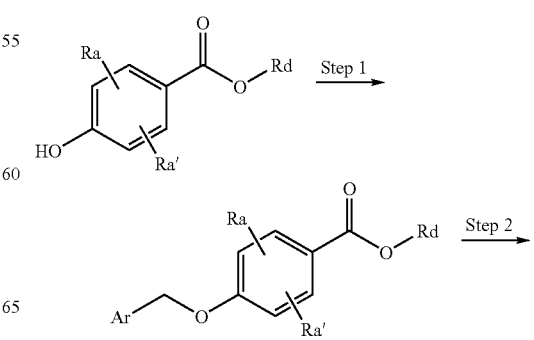

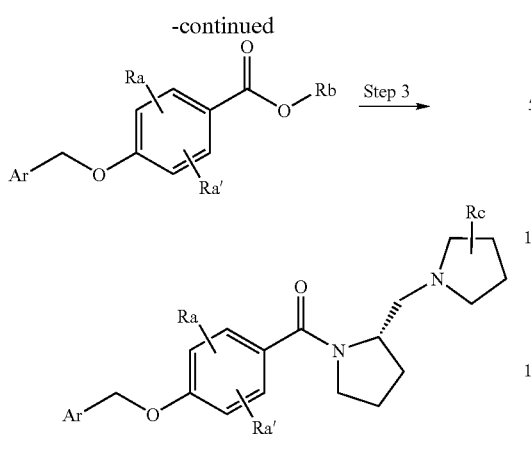

In Scheme B, $R_a$, $R_{a'}$, $R_b$, $R_c$ and Ar are as defined previously. $R_d$ can be Me, Et, Bz or butyl esters. In Scheme B (step 1), the carboxylic acid esters are alkylated by the methods described in Scheme A (step 2).

For example, Methyl 4-hydroxybenzoate, 4-(trifluoromethylthio) benzyl bromide, and $K_2CO_3$ in acetone is heated at reflux for 5 h. The mixture is cooled to room temperature and filtered. The solvent is removed to provide the benzyl ether which can be purified by well known techniques or in some cases used without purification.

In Scheme B, Step 2, the resulting esters (wherein $R_e$=Me, Et, Bz etc.), can be saponified using standard conditions to yield the corresponding carboxylic acids or the lithium, sodium or potassium salt of the acid where $R_b$ can be H, Li, Na or K. For example, to a mixture of 4-(4-Trifluoromethylsulfanyl-benzyloxy)-benzoic acid methyl ester in dioxane is added a solution of lithium hydroxide monohydrate in $H_2O$. The mixture is stirred at room temperature fro 24-48 h. The solvent is removed in vacuo to provide the crude lithium salt which is used without further purification.

In Scheme B, Step 3 the acids or the corresponding lithium, sodium or potassium salts (wherein $R_b$=H, Li, Na, K are converted to the pyrrolidinylmethylpyrrolidine amides by the methods described in Scheme A (step 1).

SCHEME C

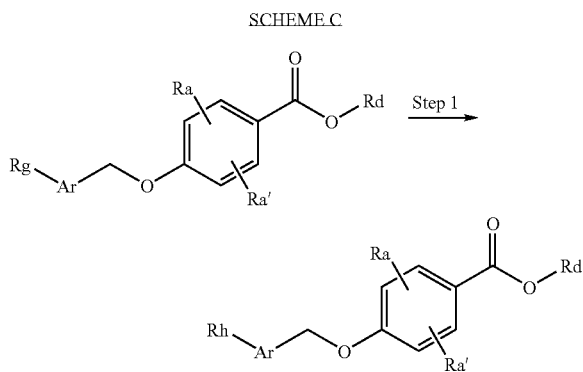

In Scheme C, $R_a$, $R_{a'}$, $R_c$, and $R_d$ are as previously defined. $R_g$ is any functional group that can be further modified to $R_h$ via alkylation, acylation, oxidation, reduction, sulfonylation, saponification etc. For example, 4-(4-Trifluoromethylsulfanyl-benzyloxy)-benzoic acid methyl ester in $CH_2Cl_2$ is added 3-chloroperoxybenzoic acid. The mixture is stirred at room temperature overnight. An aqueous solution of 1 M sodium hydroxide is added, and the mixture is extracted, concentrated, and purified according to techniques well known in the art. The esters can be converted to the pyrrolidinylmethylpyrrolidine amides by the methods described in Scheme B (step 2 and step 3).

SCHEME D

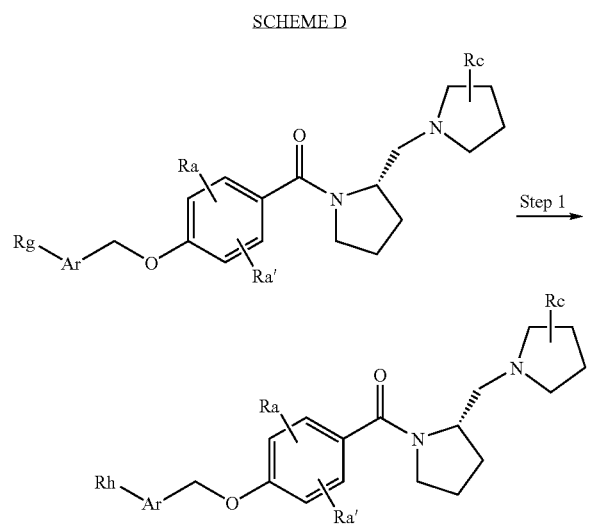

In Scheme D, $R_a$, $R_{a'}$, $R_c$, $R_g$, and $R_h$ are as previously defined. For example, [4-(2-(S)-Pyrrolidin-1-ylmethyl-pyrrolidine-1-carbonyl)-phenoxymethyl]-benzoic acid methyl ester is saponified as described in Scheme B (step 2) and converted to the corresponding cyclic amide as described by Scheme A (step 1).

Intermediate Preparation 1

(4-Hydroxy-phenyl)-(2-(S)-pyrrolidin-1-ylmethyl-pyrrolidin-1-yl)-methanone

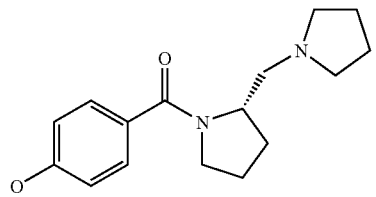

Procedure A: 4-hydroxybenzoic acid (13.5 g, 97.9 mmol) is suspended in dichloromethane (400 mL). EDC (20.0 g, 104.3 mmol) and HOBt (14.1 g, 104.3 mmol) are added at room temperature in that order. DIEA (28.4 mL, 163 mmol) and (S)(+)-1-(2-pyrrolidinylmethyl)pyrrolidine (10.0 g, 65.2 mmol) are added to the mixture. The mixture is stirred at room temperature for overnight. Water and ethyl acetate is added to the mixture. The product is water soluble necessitating a number of organic washes. The combined organic layers are dried over $Na_2SO_4$ and evaporated. The crude product is purified by silica-gel column chromatography (gradient: 100% $CH_2Cl_2$ to 10% 2M $NH_3$ in $MeOH/CH_2Cl_2$) to give the desired product (52%). MS (ES+): 275; 1H-NMR ($CDCl_3$): 7.29 (bm, 2H), 6.76 (d, 2H), 4.50 (m, 1H), 3.52 (m, 2H), 2.90 (bm, 1H), 2.70 (bm, 4H), 2.04 (bm, 1H), 1.95 (bm, 2H), 1.67 (bm, 6H).

Intermediate Preparation 2

4-[4-(2-(S)-Pyrrolidin-1-ylmethyl-pyrrolidine-1-carbonyl)-phenoxymethyl]-benzoic acid lithium salt

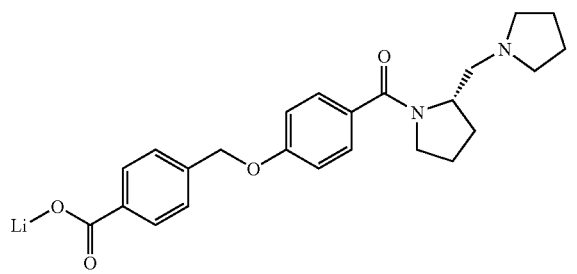

To a mixture of [4-(2-(S)-Pyrrolidin-1-ylmethyl-pyrrolidine-1-carbonyl)-phenoxymethyl]-benzoic acid methyl ester (1.14 g, 2.7 mmol) in dioxane (20 mL) is added a solution of LiOH (78 mg, 3.26 mmol) in H₂O (10 mL). The mixture is stirred at room temperature for 24 h. The solvent is removed in vacuo to provide the crude lithium salt which was used without further purification.

Intermediate Preparation 3

(2-Fluoro-4-hydroxy-phenyl)-(2-(S)-pyrrolidin-1-ylmethyl-pyrrolidin-1-yl)-methanone

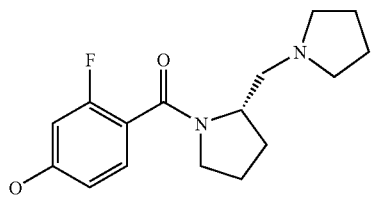

The title compound is prepared in a manner substantially analogous to Procedure
A from 2-fluoro-4-hydroxybenzoic acid [CAS 65145-13-3]. MS (ES+) 293.1

Intermediate Preparation 4

(3-Fluoro-4-hydroxy-phenyl)-(2-(S) pyrrolidin-1-ylmethyl-pyrrolidin-1-yl) methanone

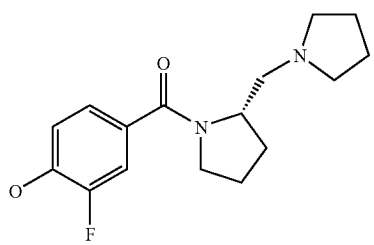

The title compound is prepared in a manner substantially analogous to Procedure A from 3-fluoro-4-hydroxybenzoic acid [CAS 350-29-8]. MS (ES+) 293.1

Intermediate Preparation 5

4-(4-Trifluoromethylsulfanyl-benzyloxy)-benzoic acid methyl ester

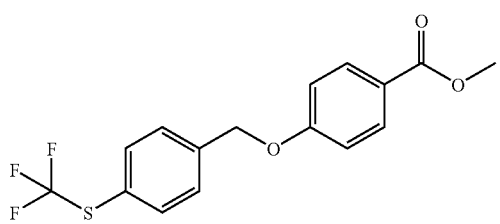

Procedure E: A mixture of methyl 4-hydroxybenzoate (2.0 g, 13.1 mmol), 4-(trifluoromethylthio) benzyl bromide (4.6 g, 17 mmol), and K₂CO₃ (4.5 g, 32.8 mmol) in acetone (70 mL) is heated at reflux for 5 h. The mixture is cooled to room temperature and filtered. The solvent is removed to provide the crude material which is used without further purification.

Intermediate Preparation 6

4-(4-Trifluoromethanesulfonyl-benzyloxy)-benzoic acid methyl ester

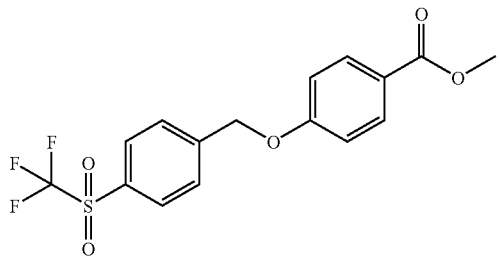

To a mixture of 4-(4-Trifluoromethylsulfanyl-benzyloxy)-benzoic acid methyl ester (1.43 g, 4.2 mmol) in CH₂Cl₂ (40 mL) is added 3-chloroperoxybenzoic acid (5.07 g, 29.4 mmol). The mixture is stirred at room temperature overnight. An aqueous solution of 1 M sodium hydroxide is added, and the mixture is extracted with EtOAc (3×). The combined organic phase is washed with brine, dried (Na₂SO₄), and concentrated to provide 1.53 g of the title compound as a white solid which is used without further purification.

Intermediate Preparation 7

4-(Pyridin-2-ylmethoxy)-benzoic acid methyl ester

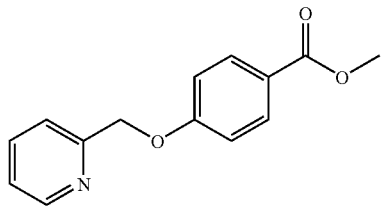

The title compound is prepared in a manner substantially analogous to Procedure E from methyl 4-hydroxybenzoate and 2-(bromomethyl)pyridine hydrobromide.

Intermediate Preparation 8

2-Fluoro-4-(pyridin-2-ylmethoxy)-benzoic acid methyl ester

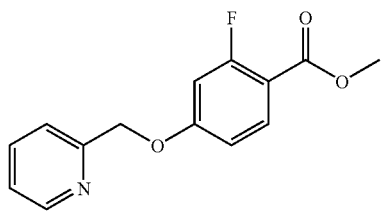

The title compound is prepared in a manner substantially analogous to Procedure E from 2-Fluoro-4-hydroxy-benzoic acid methyl ester and 2-(bromomethyl)pyridine hydrobromide. MS (ES+) 262

Intermediate Preparation 9

2,6-Difluoro-4-(pyridin-2-ylmethoxy)-benzoic acid methyl ester

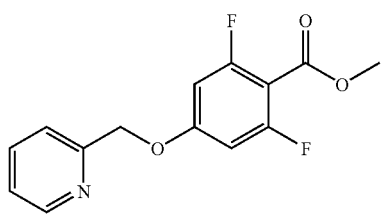

The title compound is prepared in a manner substantially analogous to Procedure E from 2,6-Difluoro-4-hydroxy-benzoic acid methyl ester and 2-(bromomethyl)pyridine hydrobromide. MS (ES+) 280

Intermediate Preparation 10

2-(R)-Methyl-1-(2-(S)-pyrrolidinylmethyl)pyrrolidine dihydrochloride salt

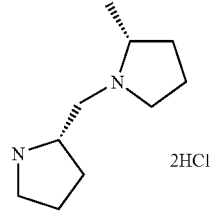

(S)-(−)-1-(tert-Butoxycarbonyl)-2-pyrrolidinemethanol (10.47 g, 52 mmol) is dissolved in 50 ml of dichloromethane. Triethylamine (8.7 mL, 62 mmol) is added, followed by slow dropwise addition of methanesulfonyl chloride (4.4 mL, 57.2 mmol). The reaction is stirred at room temperature for 4 hours and is then partitioned between ethyl acetate and water. The ethyl acetate layer is washed with 0.1 N HCl and saturated sodium bicarbonate, dried ($Na_2SO_4$), and concentrated in vacuo to give the corresponding mesylate. MS (ES+) 224 (-t-butyl), 180 (-Boc)

The crude mesylate is dissolved in THF (50 mL), and triethylamine (22 mL, 156 mmol) is added followed by R-methylpyrrolidine hydrochloride salt (CAS 135324-85-5, 9.49 g, 78 mmol), and the reaction mixture heated at 70° C. for 24 hours. The crude reaction mixture is partitioned between ethyl acetate and water. The ethyl acetate layer is washed with saturated sodium bicarbonate, dried ($Na_2SO_4$), and concentrated in vacuo to give the crude amine. Purification by flash chromatography (1-10% MeOH in $CH_2Cl_2$) affords the desired amine. MS (ES+) 269.2

The Boc protected amine is dissolved in 5 ml of 1M HCl in AcOH and stirred for 18 hours at room temperature. The mixture was then concentrated in vacuo to provide the title compound (0.95 g). MS (ES+) 169.2

Intermediate Preparation 11

2-Fluoro-4-(6-methyl-pyridin-2-ylmethoxy)-benzoic acid methyl ester

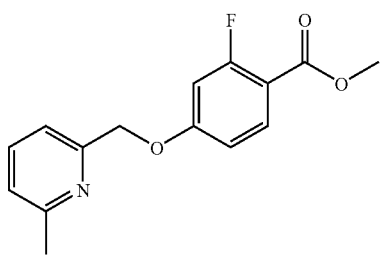

The title compound is prepared in a manner substantially analogous to Procedure E except KI (1.3 eq.) is also added from 2-Fluoro-4-hydroxy-benzoic acid methyl ester

[197507-22-5] and 2-(chloromethyl)-6-methyl-pyridine hydrochloride [CAS 3099-29-4]. MS (ES+) 276.2

Intermediate Preparation 12

4-(6-Methyl-pyridin-2-ylmethoxy)-benzoic acid methyl ester

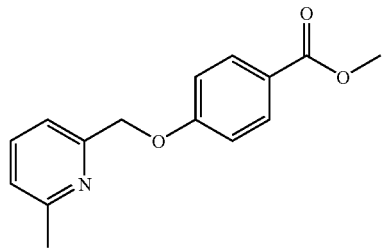

The title compound is prepared in a manner substantially analogous to Procedure E except KI (1.3 eq.) is also added from 4-hydroxy-benzoic acid methyl ester and 2-(chloromethyl)-6-methyl-pyridine hydrochloride [CAS 3099-29-4]. MS (ES+) 258.2

Intermediate Preparation 13

2-Fluoro-4-(4-methanesulfonyl-benzyloxy)-benzoic acid methyl ester

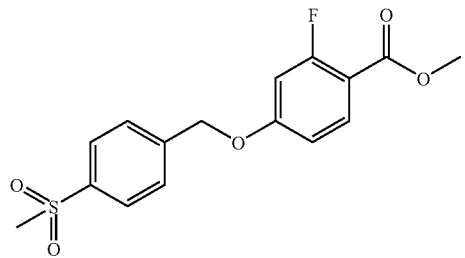

The title compound is prepared in a manner substantially analogous to Procedure E except KI (1.0 eq.) is also added from 2-fluoro-4-hydroxy-benzoic acid methyl ester [CAS 197507-22-5] and 4-methylsulfonylbenzyl chloride. $^1$H NMR (DMSO) 8.0 (d, 2H), 7.9 (t, 1H), 7.7 (d, 2H), 7.1 (dd, 1H), 7.0 (dd, 1H), 5.4 (s, 2H), 3.8 (s, 3H), 3.3 (s, 3H)

Intermediate Preparation 14

(2-Fluoro-4-hydroxy-phenyl)-[2-(S)(2-(R)-methyl-pyrrolidin-1-ylmethyl)-pyrrolidin-1-yl]-methanone

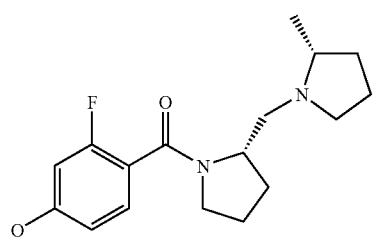

The title compound is prepared in a manner substantially analogous to Procedure A from 2-fluoro-4-hydroxybenzoic acid and 2-(R)-Methyl-1-(2-(S)-pyrrolidinylmethyl)pyrrolidine. MS (ES+) 307.3

Intermediate Preparation 15

2-Fluoro-4-(4-trifluoromethanesulfonyl-benzyloxy)-benzoic acid methyl ester

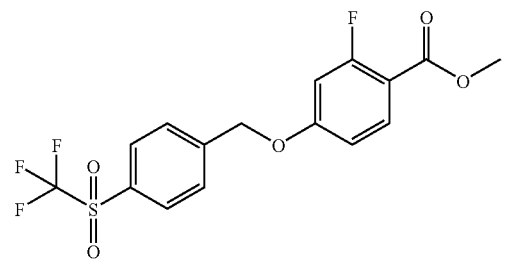

The title compound is prepared in a manner substantially analogous to Procedure E and Intermediate Preparation 6 from 2-fluoro-4-hydroxy-benzoic acid methyl ester [CAS 197507-22-5] and 4-(trifluoromethylthio)benzyl bromide. MS (ES+) 393.2

Intermediate Preparation 16

2-(R)-Methyl-1-(2-(S)-pyrrolidinylmethyl)pyrrolidine

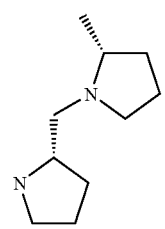

(S) BOC proline (CAS 15761-394) and 2-(R)-Methyl-pyrrolidine hydrochloride (CAS 135324-85-5) are coupled in a manner substantially analogous to Procedure A in dichloromethane to give 2(S)-(2(R)-Methyl-pyrrolidine-1-carbonyl)-pyrrolidine-1-carboxylic acid tert-butyl ester. The material is deprotected by stirring in dichloromethane at 5-10° C. while trifluoroacetic acid (10 eq,) is added and then stirred at room temperature for 18 hours. Reaction is concentrated, is dissolved in H$_2$O, pH is adjusted to 8-9 with K$_2$CO$_3$, and is extracted several times with CH$_2$Cl$_2$. The extracts are combined, dried (Na$_2$SO$_4$) and concentrated in vacuo to give (2(R)-Methyl-pyrrolidin-1-yl)-pyrrolidin-2-yl-methanone.

A 1 M Lithium Aluminum Hydride/THF solution (3 eq.) is diluted with an equal volume of THF and stirred under N$_2$ as a THF solution of (2(R)-methyl-pyrrolidin-1-yl)-pyrrolidin-2-yl-methanone is added dropwise, allowing the reaction to mildly exotherm. The reaction mixture is stirred at 40° C. for 45 minutes, then at room temperature 18 hours. The mixture is cooled in an ice bath and is quenched with H$_2$O (3 eq.), 4 N NaOH (3 eq.), then H$_2$O (9 eq.) while keeping reaction temperature less than 15° C. The mixture is stirred overnight, filtered and the precipitate is washed three times with THF. The filtrate and washes are combined and concentrated to give 2-(R)-methyl-1-(2-(S)-pyrrolidinylmethyl)pyrrolidine. MS (ES+) 169.3 (M+H)⁺ The title compound is used as such or is purified by SCX chromatography or distillation.

EXAMPLE 1

(4-Benzyloxy-phenyl)-(2-(S)-pyrrolidin-1-ylmethyl-pyrrolidin-1-yl)-methanone

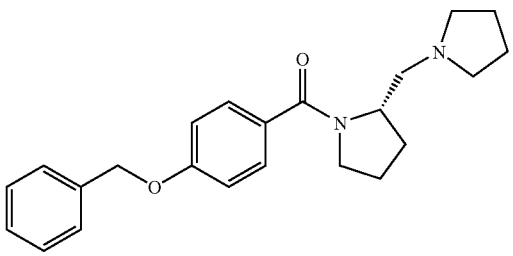

To a suspension of 4-benzyloxybenzoic acid (116 mg, 0.51 mmol) and PS-carbodiimide (500 mg, 0.66 mmol, 1.32 mmol/g) in 5% DMF in $CH_2Cl_2$ (5 mL) is added (S)(+)-1-(2-pyrrolidinylmethyl)pyrrolidine (80 mg, 0.51 mmol). The mixture is stirred at room temperature for 3 days. The reaction mixture is filtered, and the resin is washed with $CH_2Cl_2$. The filtrate is concentrated and applied to silica-gel column chromatography (in $CH_2Cl_2$ followed by 5% 2M $NH_3$ in MeOH/$CH_2Cl_2$) to give the product. 62.7 mg (34%): Observed mass: 365 (M+1).

Procedure B: A mixture of (4-Hydroxy-phenyl)-(2-(S)-pyrrolidin-1-ylmethyl-pyrrolidin-1-yl)-methanone (100 mg, 0.36 mmol), $Cs_2CO_3$ (0.24 g, 0.73 mmol), and the appropriate alkyl bromide (0.43 mmol) in DMF (5 mL) is stirred at room temperature overnight. The mixture is partitioned with EtOAc and $H_2O$. The aqueous phase is extracted with EtOAc (2×). The combined organic phase is dried ($Na_2SO_4$) and concentrated. The crude product is purified by reverse phase chromatography to provide the desired product as a trifluoroacetate salt.

The following examples are prepared in a manner substantially analogous to Procedure B starting from the appropriate materials;

| Example | Structure | MS(ES+) |
|---|---|---|
| 2 | ![structure] 3-[4-(2-(S)-pyrrolidin-1-ylmethyl-pyrrolidine-1-carbonyl)-phenoxymethyl]-benzonitrile trifluoroacetate | 390.3 |
| 3 | ![structure] (2-(S)-pyrrolidin-1-ylmethyl-pyrrolidin-1-yl)-[4-(3-trifluoromethoxy-benzyloxy)-phenyl]-methanone trifluoroacetate | 449.3 |

-continued

| Example | Structure | MS(ES+) |
|---|---|---|
| 4 | [4-(3-Methoxy-benzyloxy)-phenyl]-(2-(S)-pyrrolidin-1-ylmethyl-pyrrolidin-1-yl)-methanone trifluoroacetate | 395.3 |
| 5 | (2-(S)-pyrrolidin-1-ylmethyl-pyrrolidin-1-yl)-[4-(3-trifluoromethyl-benzyloxy)-phenyl]-methanone trifluoroacetate | 433.4 |
| 6 | (2-(S)-pyrrolidin-1-ylmethyl-pyrrolidin-1-yl)-[4-(4-trifluoromethyl-benzyloxy)-phenyl]-methanone | 433.4 |
| 7 | [4-(4-Methyl-benzyloxy)-phenyl]-(2-(S)-pyrrolidin-1-ylmethyl-pyrrolidin-1-yl)-methanone trifluoroacetate | 379.4 |

| Example | Structure | MS(ES+) |
|---|---|---|
| 8 | 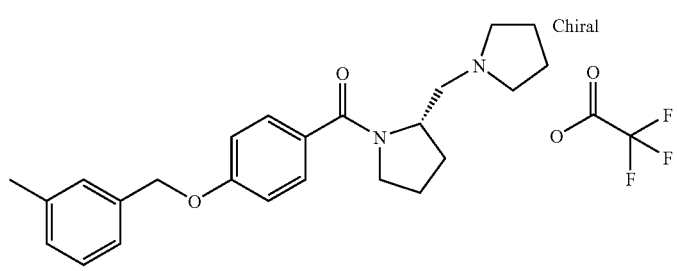<br>[4-(3-Methyl-benzyloxy)-phenyl]-(2-(S)-pyrrolidin-1-ylmethyl-pyrrolidin-1-yl)-methanone trifluoroacetate | 379.4 |
| 9 | 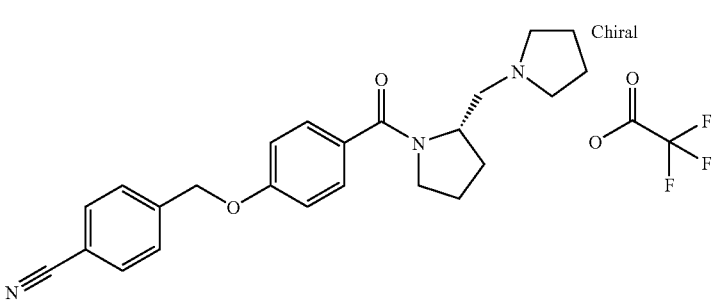<br>4-[4-(2-(S)-pyrrolidin-1-ylmethyl-pyrrolidine-1-carbonyl)-phenoxymethyl]-benzonitrile trifluoroacetate | 390.4 |
| 10 | 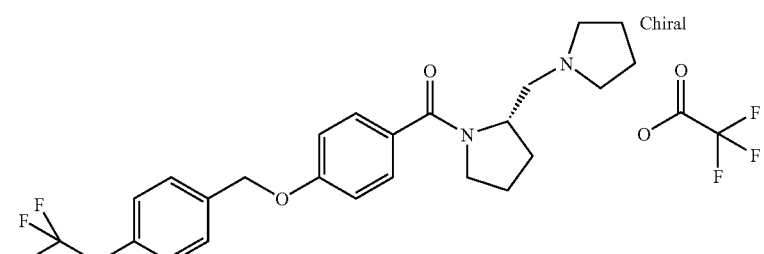<br>(2-(S)-pyrrolidin-1-ylmethyl-pyrrolidin-1-yl)-[4-(4-trifluoromethoxy-benzyloxy)-phenyl]-methanone trifluoroacetate | 449.4 |
| 11 | 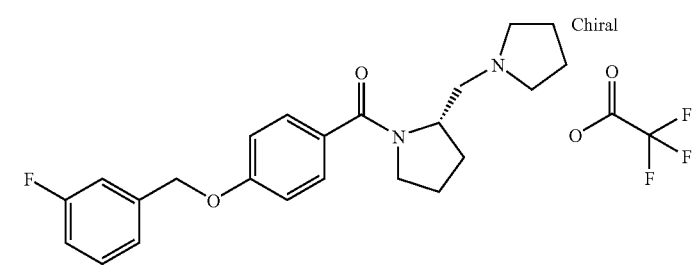<br>[4-(3-Fluoro-benzyloxy)-phenyl]-(2-(S)-pyrrolidin-1-ylmethyl-pyrrolidin-1-yl)-methanone trifluoroacetate | 383.4 |

-continued

| Example | Structure | MS(ES+) |
|---|---|---|
| 12 | 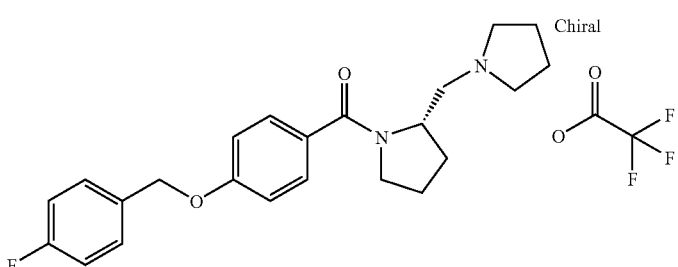 [4-(4-Fluoro-benzyloxy)-phenyl]-(2-(S)-pyrrolidin-1-ylmethyl-pyrrolidin-1-yl)-methanone trifluoroacetate | 383.4 |
| 13 | 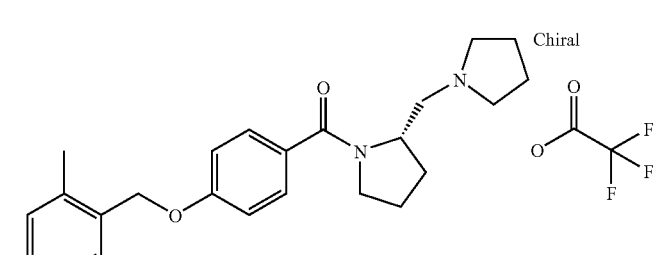 [4-(2-Methyl-benzyloxy)-phenyl]-(2-(S)-pyrrolidin-1-ylmethyl-pyrrolidin-1-yl)-methanone trifluoroacetate | 379.4 |
| 14 | 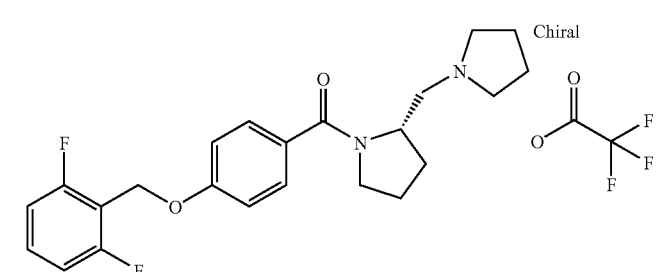 [4-(2,6-Difluoro-benzyloxy)-phenyl]-(2-(S)-pyrrolidin-1-ylmethyl-pyrrolidin-1-yl)-methanone trifluoroacetate | 401.4 |
| 15 | 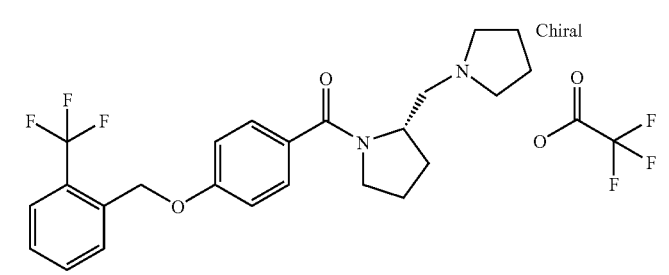 (2-(S)-pyrrolidin-1-ylmethyl-pyrrolidin-1-yl)-[4-(2-trifluoromethyl-benzyloxy)-phenyl]-methanone trifluoroacetate | 433.4 |

| Example | Structure | MS(ES+) |
|---|---|---|
| 16 | [4-(2-Benzenesulfonylmethyl-benzyloxy)-phenyl]-(2-(S)-pyrrolidin-1-ylmethyl-pyrrolidin-1-yl)-methanone trifluoroacetate | 519.4 |
| 17 | [4-(4-Benzoyl-benzyloxy)-phenyl]-(2-(S)-pyrrolidin-1-ylmethyl-pyrrolidin-1-yl)-methanone | 469.2 |

EXAMPLE 18

[4-(Pyridin-3-ylmethoxy)-phenyl]-(2-(S)-pyrrolidin-1-ylmethyl-pyrrolidin-1-yl)-methanone

EXAMPLE 19

[4-(Pyridin-4-ylmethoxy)-phenyl]-(2-(S)-pyrrolidin-1-ylmethyl-pyrrolidin-1-yl)-methanone

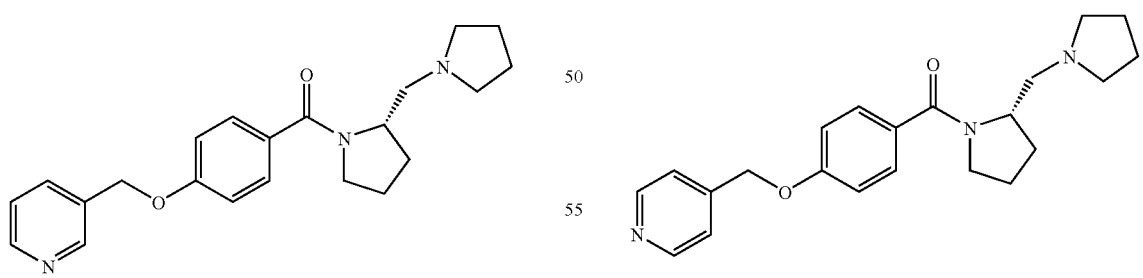

The title compound is prepared in a manner substantially analogous to Procedure B using (4-Hydroxy-phenyl)-(2-(S)-pyrrolidin-1-ylmethyl-pyrrolidin-1-yl)-methanone and 3-(bromomethyl)pyridine hydrobromide. MS (ES+) 366.2

The title compound is prepared in a manner substantially analogous to Procedure B using (4-Hydroxy-phenyl)-(2-(S)-pyrrolidin-1-ylmethyl-pyrrolidin-1-yl)-methanone and 4-(bromomethyl)pyridine hydrobromide. MS (ES+) 366.2

EXAMPLE 20

[4-(4-Methanesulfonyl-benzyloxy)-phenyl]-(2-(S)-pyrrolidin-1-ylmethyl-pyrrolidin-1-yl)-methanone

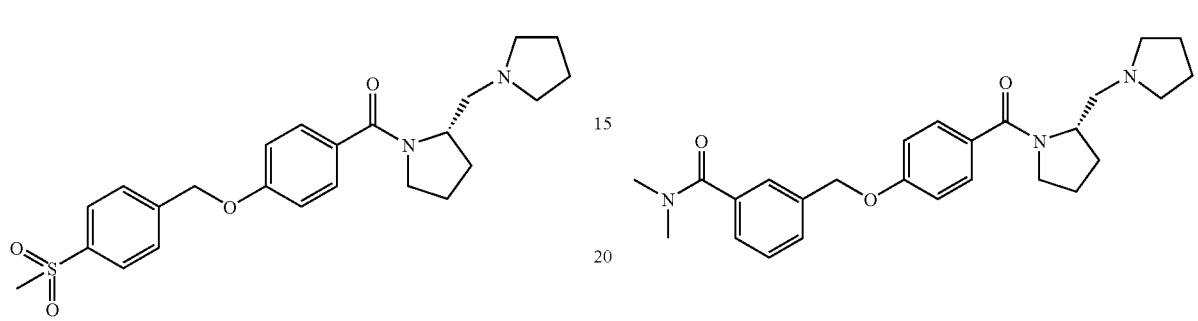

Procedure C: A mixture of (4-Hydroxy-phenyl)-(2(S)-pyrrolidin-1-ylmethyl-pyrrolidin-1-yl)-methanone (1.23 g, 4.5 mmol), $Cs_2CO_3$ (2.2 g, 6.8 mmol), KI (0.75 g, 4.5 mmol) and 4-methylsulfonylbenzyl chloride (1.0 g, 5.1 mmol) in DMF (15 mL) is stirred at room temperature overnight. The mixture is partitioned between EtOAc and $H_2O$. The aqueous phase is extracted with EtOAc (2×). The combined organic phase is dried ($Na_2SO_4$) and concentrated. The crude product is purified by silica-gel column chromatography. MS (ES+) 443.2

EXAMPLE 21

N,N-Dimethyl-4-[4-(2-(S)-pyrrolidin-1-ylmethyl-pyrrolidine-1-carbonyl)-phenoxymethyl]-benzamide The title compound is prepared in a manner substantially analogous to Procedure C using (4-Hydroxy-phenyl)-(2-(S)-pyrrolidin-1-ylmethyl-pyrrolidin-1-yl)-methanone and 4-chloromethyl-N,N-dimethyl-benzamide [CAS 121083-51-0]. MS (ES+) 436.3

EXAMPLE 22

N,N-Dimethyl-3-[4-(2-(S)-pyrrolidin-1-ylmethyl-pyrrolidine-1-carbonyl)-phenoxymethyl]-benzamide

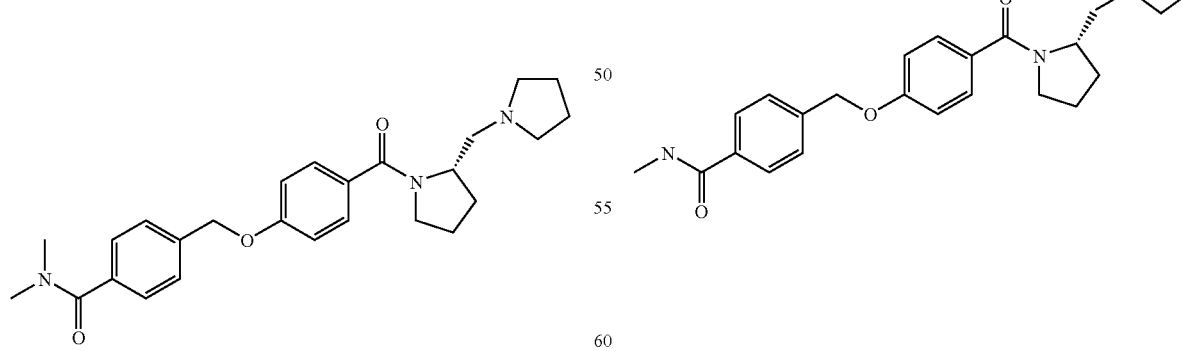

The title compound is prepared in a manner substantially analogous to Procedure C using (4-Hydroxy-phenyl)-(2-(S)-pyrrolidin-1-ylmethyl-pyrrolidin-1-yl)-methanone and 3-chloromethyl-N,N-dimethyl-benzamide [CAS 442910-26-1]. MS (ES+) 436.3

EXAMPLE 23

N-Methyl-4-[4-(2-(S)-pyrrolidin-1-ylmethyl-pyrrolidine-1-carbonyl)-phenoxymethyl]-benzamide The title compound is prepared in a manner substantially analogous to Procedure C using (4-Hydroxy-phenyl)-(2-(S)-pyrrolidin-1-ylmethyl-pyrrolidin-1-yl)-methanone and 4-chloromethyl-N-methyl-benzamide [CAS 220875-88-7]. MS (ES+) 422.2

EXAMPLE 24

(2-(S)-Pyrrolidin-1-ylmethyl-pyrrolidin-1-yl)-[4-(6-trifluoromethyl-pyridin-3-ylmethoxy)-phenyl]-methanone

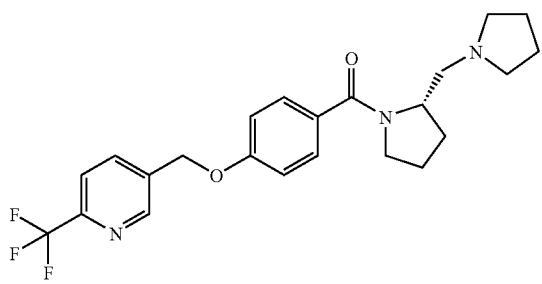

The title compound is prepared in a manner substantially analogous to Procedure C using (4-Hydroxy-phenyl)-(2-(S)-pyrrolidin-1-ylmethyl-pyrrolidin-1-yl)-methanone and 3-(chloromethyl)-6-(trifluoromethyl)pyridine. MS (ES+) 434.2

EXAMPLE 25

[4-(6-Chloro-pyridin-3-ylmethoxy)-phenyl]-(2-(S)-pyrrolidin-1-ylmethyl-pyrrolidin-1-yl)-methanone

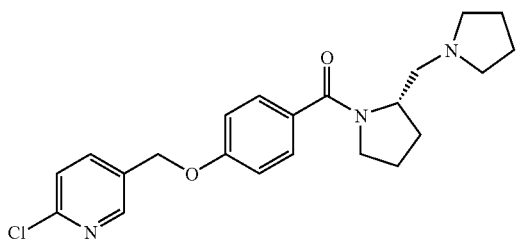

The title compound is prepared in a manner substantially analogous to Procedure C using (4-Hydroxy-phenyl)-(2-(S)-pyrrolidin-1-ylmethyl-pyrrolidin-1-yl)-methanone and 2-chloro-5-(chloromethyl)pyridine [CAS 70258-18-3]. MS (ES+) 400.2

EXAMPLE 26

[4-(4-Methoxy-benzyloxy)-phenyl]-(2-(S)-pyrrolidin-1-ylmethyl-pyrrolidin-1-yl)-methanone Trifluoroacetate

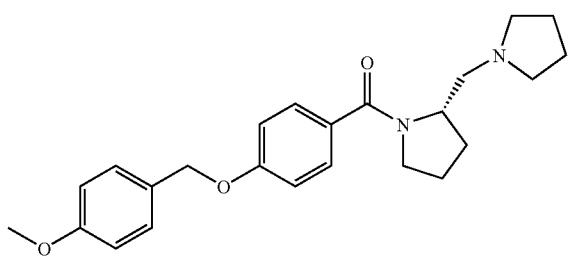

-continued

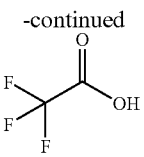

The title compound is prepared in a manner substantially analogous to Procedure C using (4-Hydroxy-phenyl)-(2-(S)-pyrrolidin-1-ylmethyl-pyrrolidin-1-yl)-methanone and 4-methoxy benzyl chloride except reverse phase chromatography is used for purification. MS (ES+) 395.2

EXAMPLE 27

(2-(S)-Pyrrolidin-1-ylmethyl-pyrrolidin-1-yl)-[4-(2-trifluoromethoxy-benzyloxy)-phenyl]-methanone Trifluoroacetate

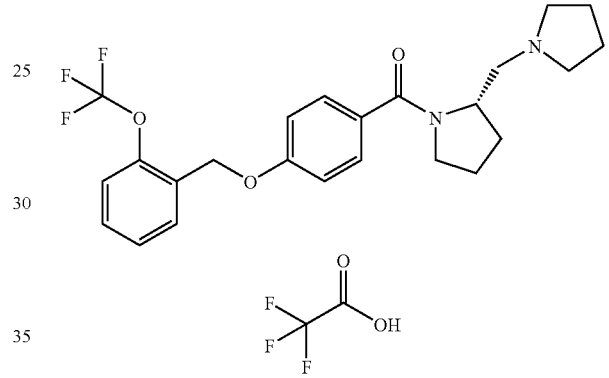

The title compound is prepared in a manner substantially analogous to Procedure C using (4-Hydroxy-phenyl)-(2-(S)-pyrrolidin-1-ylmethyl-pyrrolidin-1-yl)-methanone and (1-chloromethyl)-2-trifluoromethoxybenzene except reverse phase chromatography is used for purification. MS (ES+) 449.2

EXAMPLE 28

4-[4-(2-(S)-Pyrrolidin-1-ylmethyl-pyrrolidine-1-carbonyl)-phenoxymethyl]-benzoic acid methyl ester

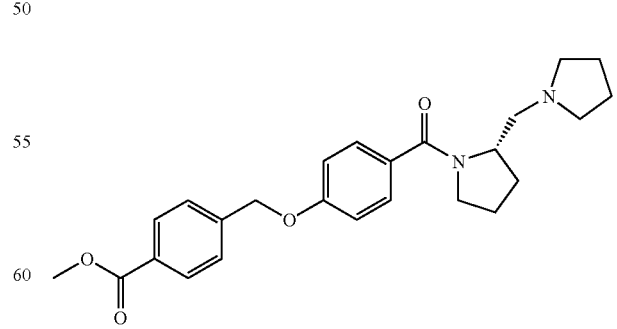

The title compound is prepared in a manner substantially analogous to Procedure B using (4-Hydroxy-phenyl)-(2-(S)-pyrrolidin-1-ylmethyl-pyrrolidin-1-yl)-methanone and methyl 4-(bromomethyl)benzoate. MS (ES+) 423.3

EXAMPLE 29

{4-[4-(Pyrrolidine-1-carbonyl)-benzyloxy]-phenyl}-(2-(S)-pyrrolidin-1-ylmethyl-pyrrolidin-1-yl)-methanone Procedure D: To a mixture of 4-[4-(2-(S)-Pyrrolidin-1-ylmethyl-pyrrolidine-1-carbonyl)-phenoxymethyl]-benzoic acid lithium salt (0.2 g, 0.48 mmol) in dichloromethane (5 mL) is added EDC (0.11 g, 0.58 mmol) and HOBt (78 mg, 0.58 mmol). DIEA (0.37 mL, 0.96 mmol) and pyrrolidine (34 µL, 0.41 mmol) are added to the mixture. The mixture is stirred at room temperature overnight. The mixture is partitioned between H$_2$O and EtOAc. The aqueous phase is extracted with EtOAc (2×), and the combined organic phase is dried (Na$_2$SO$_4$) and evaporated. The crude product is purified by silica-gel column chromatography. MS (ES+) 462.3

EXAMPLE 30

{4-[4-(Azetidine-1-carbonyl)-benzyloxy]-phenyl}-(2-(S)-pyrrolidin-1-ylmethyl-pyrrolidin-1-yl)-methanone The title compound is prepared in a manner substantially analogous to Procedure D from 4-[4-(2-(S)-Pyrrolidin-1-yl-methyl-pyrrolidine-1-carbonyl)-phenoxymethyl]-benzoic acid lithium salt and azetidine. MS (ES+) 448.2

EXAMPLE 31

{4-[4-(Piperidine-1-carbonyl)-benzyloxy]-phenyl}-(2-(S)-pyrrolidin-1-ylmethyl-pyrrolidin-1-yl)-methanone The title compound is prepared in a manner substantially analogous to Procedure D from 4-[4-(2-(S)-Pyrrolidin-1-yl-methyl-pyrrolidine-1-carbonyl)-phenoxymethyl]-benzoic acid lithium salt and piperidine. MS (ES+) 476.2

EXAMPLE 32

[2-Fluoro-4-(4-methanesulfonyl-benzyloxy)-phenyl]-(2-(S)-pyrrolidin-1-ylmethyl-pyrrolidin-1-yl)-methanone The title compound is prepared in a manner substantially analogous to Procedure C from (2-Fluoro-4-hydroxy-phenyl)-(2-(S)-pyrrolidin-1-ylmethyl-pyrrolidin-1-yl)-methanone and 4-methylsulfonylbenzyl chloride. MS (ES+) 461.2

EXAMPLE 33

4-[3-Fluoro-4-(2-(S)-pyrrolidin-1-ylmethyl-pyrrolidine 1-carbonyl)-phenoxymethyl]-N,N-dimethyl-benzamide

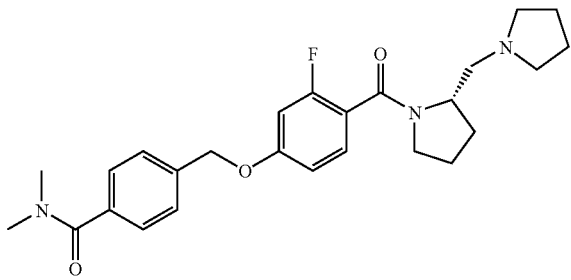

The title compound is prepared in a manner substantially analogous to Procedure C using (2-Fluoro-4-hydroxy-phenyl)-(2-(S)-pyrrolidin-1-ylmethyl-pyrrolidin-1-yl)-methanone and 4-chloromethyl-N,N-dimethyl-benzamide [CAS 121083-51-0]. MS (ES+) 454.2

EXAMPLE 34

[2-Fluoro-4-(pyridin-4-ylmethoxy)-phenyl]-(2-(S)-pyrrolidin-1-ylmethyl-pyrrolidin-1-yl)-methanone

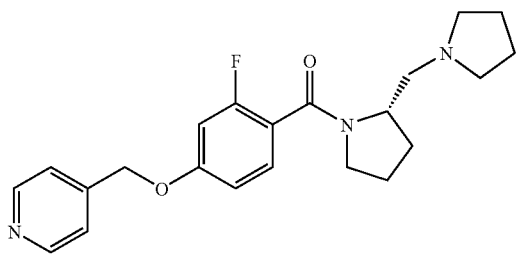

The title compound is prepared in a manner substantially analogous to Procedure B using (2-Fluoro-4-hydroxy-phenyl)-(2-(S)-pyrrolidin-1-ylmethyl-pyrrolidin-1-yl)-methanone and 4-(bromomethyl)pyridine hydrobromide. MS (ES+) 384.2

EXAMPLE 35

[4-(6-Chloro-pyridin-3-ylmethoxy)-2-fluoro-phenyl]-(2-(S)-pyrrolidin-1-ylmethyl-pyrrolidin-1-yl)-methanone

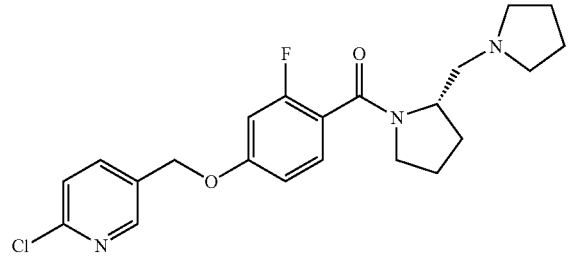

The title compound is prepared in a manner substantially analogous to Procedure C using (2-Fluoro-4-hydroxy-phenyl)-(2-(S)-pyrrolidin-1-ylmethyl-pyrrolidin-1-yl)-methanone and 2-chloro-5-(chloromethyl)pyridine [CAS 70258-18-3]. MS (ES+) 418.3

EXAMPLE 36

[2-Fluoro-4-(4-fluoro-benzyloxy)-phenyl]-(2-(S)-pyrrolidin-1-ylmethyl-pyrrolidin-1-yl)-methanone

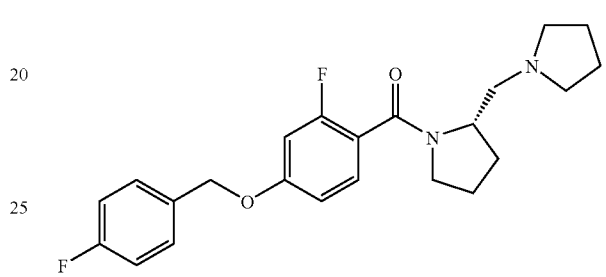

The title compound is prepared in a manner substantially analogous to Procedure B using (2-Fluoro-4-hydroxy-phenyl)-(2-(S)-pyrrolidin-1-ylmethyl-pyrrolidin-1-yl)-methanone and 4-fluorobenzyl bromide. MS (ES+) 401.2

EXAMPLE 37

[3-Fluoro-4-(4-methanesulfonyl-benzyloxy)-phenyl]-(2-(S)-pyrrolidin-1-ylmethyl-pyrrolidin-1-yl)-methanone

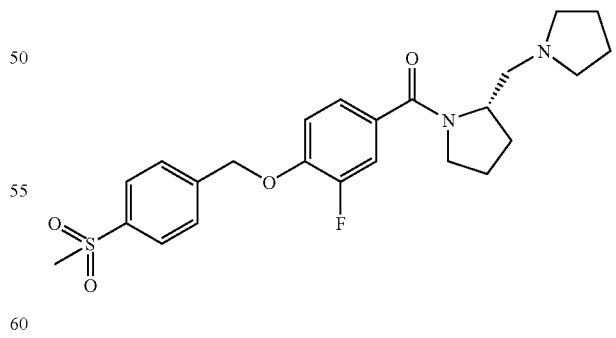

The title compound is prepared in a manner substantially analogous to Procedure C from (3-Fluoro-4-hydroxy-phenyl)-(2-(S)-pyrrolidin-1-ylmethyl-pyrrolidin-1-yl)methanone and 4-methylsulfonylbenzyl chloride. MS (ES+) 461.2

EXAMPLE 38

4-[2-Fluoro-4-(2-(S)-pyrrolidin-1-ylmethyl-pyrrolidine-1-carbonyl)-phenoxymethyl]-N,N-dimethyl-benzamide

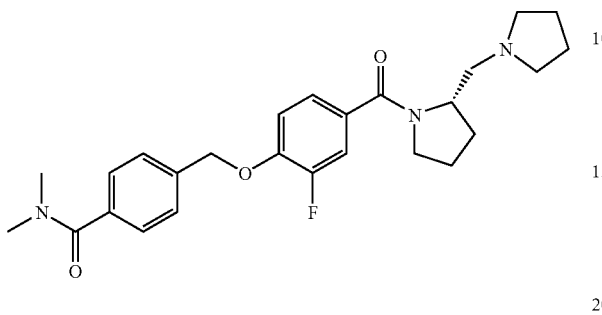

The title compound is prepared in a manner substantially analogous to Procedure C from (3-Fluoro-4-hydroxy-phenyl)-(2-(S)-pyrrolidin-1-ylmethyl-pyrrolidin-1-yl)methanone and 4-chloromethyl-N,N-dimethyl-benzamide [CAS 121083-51-0]. MS (ES+) 454.2

EXAMPLE 39

(2-(S)-Pyrrolidin-1-ylmethyl-pyrrolidin-1-yl)-[4-(4-trifluoromethylsulfanyl-benzyloxy)-phenyl]-methanone

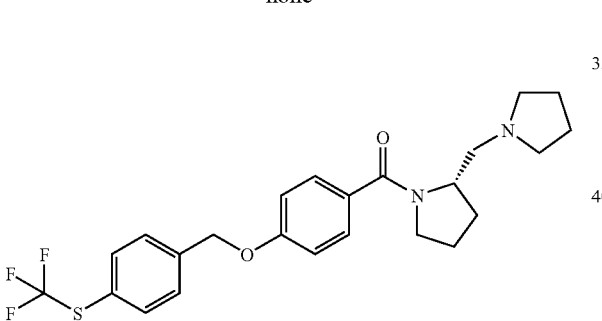

Procedure F: To a mixture of 4-(4-Trifluoromethylsulfanyl-benzyloxy)-benzoic acid methyl ester (0.33 g, 0.96 mmol) in dioxane (10 mL) is added a solution of lithium hydroxide monohydrate (48 mg, 1.15 mmol) in $H_2O$ (5 mL). The mixture is stirred at room temperature overnight. Reaction is not complete so additional lithium hydroxide monohydrate (48 mg, 1.15: mmol) in $H_2O$ (5 mL) is added. The mixture is stirred at room temperature for 6 h. The solvent is removed in vacuo to provide the crude lithium salt which is used without further purification.

To a mixture of 4-(4-Trifluoromethylsulfanyl-benzyloxy)-benzoic acid lithium salt in dichloromethane (20 mL) and DMF (5 mL) is added EDC (0.22 g, 1.2 mmol), HOBt (0.16 g, 1.2 mmol), and DIEA (0.35 ml, 1.9 mmol). After a few minutes, (S)(+)-1-(2-pyrrolidinylmethyl)pyrrolidine (0.19 mL, 1.2 mmol) is added, and the mixture is stirred at room temperature overnight. The mixture is partitioned between water and ethyl acetate, and the aqueous phase is extracted with ethyl acetate (2x). The combined organic phase is dried ($Na_2SO_4$) and evaporated. The crude product is purified by silica-gel column chromatography. MS (ES+) 465.2

EXAMPLE 40

(2-(S)-Pyrrolidin-1-ylmethyl-pyrrolidin-1-yl)-[4-(4-trifluoromethanesulfonyl-benzyloxy)-phenyl]-methanone

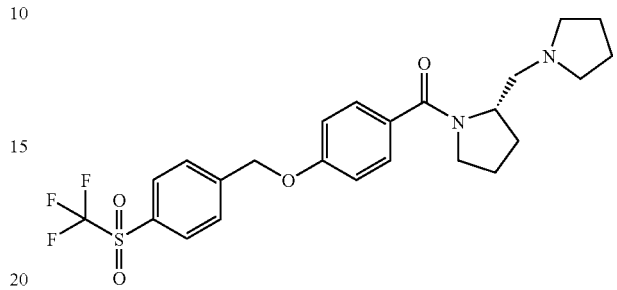

The title compound is prepared in a manner substantially analogous to Procedure F from 4-(4-Trifluoromethanesulfonyl-benzyloxy)-benzoic acid methyl ester. MS (ES+) 497.2

EXAMPLE 41

[4-(Pyridin-2-ylmethoxy)-phenyl]-(2-(S)-pyrrolidin-1-ylmethyl-pyrrolidin-1-yl)-methanone

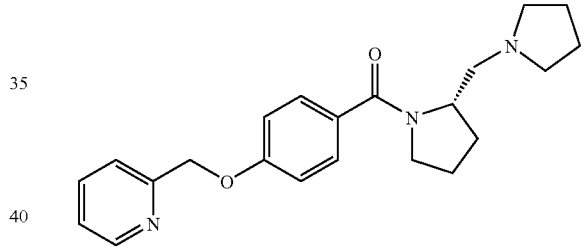

The title compound is prepared in a manner substantially analogous to Procedure F from 4-(Pyridin-2-ylmethoxy)-benzoic acid methyl ester. MS (ES+) 366

EXAMPLE 42

[4-(Pyridin-2-ylmethoxy)-phenyl]-(2-(S)-pyrrolidin-1-ylmethyl-pyrrolidin-1-yl)-methanone dihydrochloric acid salt

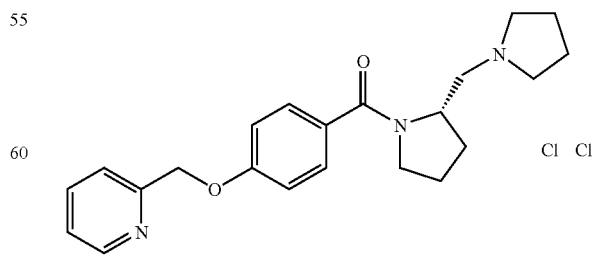

To a solution of [4-(Pyridin-2-ylmethoxy)-phenyl]-(2-(S)-pyrrolidin-1-ylmethyl-pyrrolidin-1-yl)-methanone (1.94 g, 5.3 mmol) in diethyl ether and methanol is added a solution of HCl in ether (10.7 mmol, 1M). The mixture is concentrated, and the oily residue is dissolved in a mixture of diethyl ether and methanol and again concentrated. The solid is triturated with petroleum ether, and the solid is dried to yield 2.2 g of a yellowish solid MS (ES+) 1366.3

EXAMPLE 43

[4-(4-Fluoro-benzyloxy)-phenyl]-(2-(S)-pyrrolidin-)-ylmethyl-pyrrolidin-1-yl)-methanone hydrochloride salt

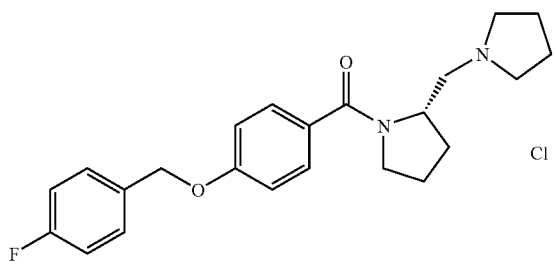

[4-(4-Fluoro-benzyloxy)-phenyl]-(2-(S)-pyrrolidin-1-ylmethyl-pyrrolidin-1-yl)-methanone (0.165 g, 0.43 mmol) is suspended in diethyl ether, and methanol is added dropwise until the solid dissolves. A solution of 1M HCl in diethyl ether (0.43 mmol) is added, and the mixture is concentrated and dried. MS (ES+) 383

EXAMPLE 44

[2-Fluoro-4-(pyridin-2-ylmethoxy)-phenyl]-(2-(S)-pyrrolidin-1-ylmethyl-pyrrolidin-1-yl)-methanone

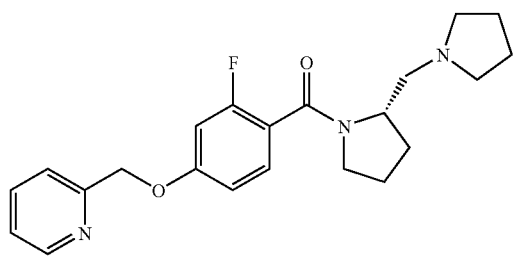

The title compound is prepared in a manner substantially analogous to Procedure F from 2-Fluoro-4-(pyridin-2-ylmethoxy)-benzoic acid methyl ester. MS (ES+) 384

EXAMPLE 45

[2-Fluoro-4-(pyridin-2-ylmethoxy)-phenyl]-(2-(S)-pyrrolidin-1-ylmethyl-pyrrolidin-1-yl)-methanone dihydrochloride salt

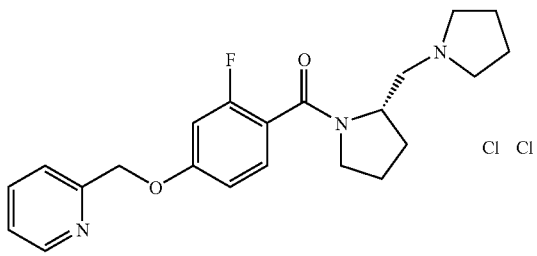

To a solution of [2-Fluoro-4-(pyridin-2-ylmethoxy)-phenyl]-(2-(S)-pyrrolidin-1-ylmethyl-pyrrolidin-1-yl)-methanone (0.386 g, 1 mmol) in methanol (3 mL) is added a solution of 4M HCl in dioxane (2 mmol). The mixture is concentrated, and the oily residue is dissolved in $CH_2Cl_2$ and again concentrated and dried. MS (ES+) 384

EXAMPLE 46

[2,6-Difluoro-4-(pyridin-2-ylmethoxy)-phenyl]-(2-(S)-pyrrolidin-1-ylmethyl-pyrrolidin-1-yl)-methanone

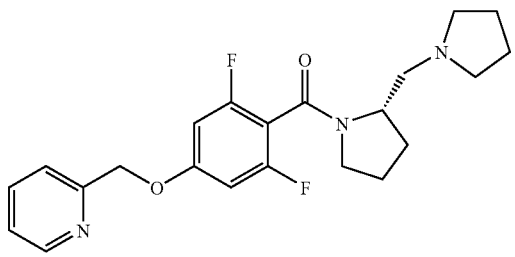

The title compound is prepared in a manner substantially analogous to Procedure F from 2,6-Difluoro-4-(pyridin-2-ylmethoxy)-benzoic acid methyl ester. MS (ES+) 402.2

EXAMPLE 47

[2-Fluoro-4-(pyridin-2-ylmethoxy)-phenyl]-[2-(S)-(2-(R)-methyl-pyrrolidin-1-ylmethyl)-pyrrolidin-1-yl]-methanone

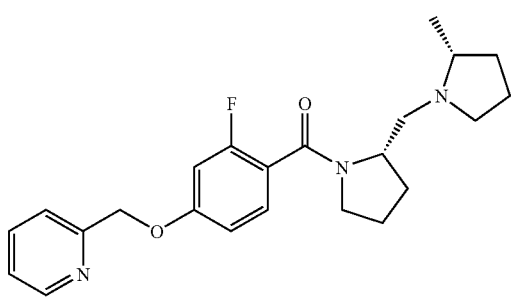

The title compound is prepared in a manner substantially analogous to Procedure A from 2-Fluoro-4-(pyridin-2-yl-methoxy)-benzoic acid lithium salt and 2-(R)-Methyl-1-(2-(S)-pyrrolidinylmethyl)pyrrolidine dihydrochloride salt. MS (ES+) 398.3

EXAMPLE 48

[4-(Pyrazin-2-ylmethoxy)-phenyl]-(2-(S)-pyrrolidin-1-ylmethyl-pyrrolidin-1-yl)-methanone

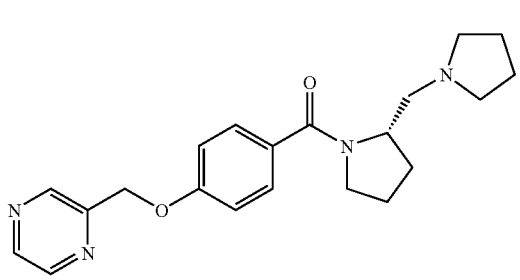

To a mixture of (4-Hydroxy-phenyl)-(2-(S)-pyrrolidin-1-ylmethyl-pyrrolidin-1-yl)-methanone (0.57 g, 2.0 mmol), pyrazin-2-yl-methanol [CAS 6705-33-5] (0.25 g, 2.3 mmol), and triphenylphosphine (0.57 g, 2.2 mmol) in THF (20 mL) is added DEAD (0.36 mL, 2.3 mmol). The mixture is stirred at room temperature overnight and partitioned between ethyl acetate and water. The aqueous phase is extracted with ethyl acetate (2×), and the combined organic phase is dried ($Na_2SO_4$) and concentrated. The crude material is purified by SCX chromatography followed by silica gel chromatography eluting with 20% (10% 2M MeOH/$CH_2Cl_2$)/80% $CH_2Cl_2$ to 70% (10% 2M MeOH/$CH_2Cl_2$)/30% $CH_2Cl_2$ to yield 12 mg of the title compound. MS (ES+) 367.3

EXAMPLE 49

4-[4-(2-(S)-Pyrrolidin-1-ylmethyl-pyrrolidine-1-carbonyl)-phenoxymethyl]-benzoic acid lithium salt

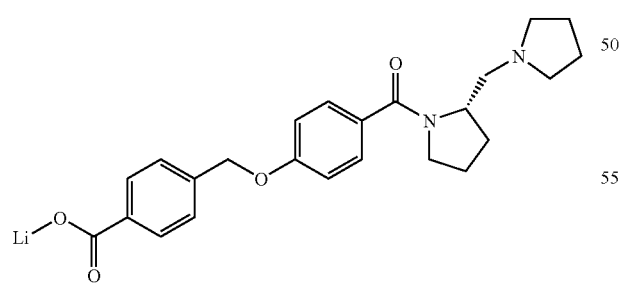

To a mixture of [4-(2-(S)-Pyrrolidin-1-ylmethyl-pyrrolidine-1-carbonyl)-phenoxymethyl]-benzoic acid methyl ester (1.14 g, 2.7 mmol) in dioxane (20 mL) is added a solution of LiOH (78 mg, 3.26 mmol) in $H_2O$ (10 mL). The mixture is stirred at room temperature for 24 h. The solvent is removed in vacuo to provide the crude lithium salt which is further purified according to methods known in the art. See also Intermediate Preparation 2.

EXAMPLE 50

[2,6-Difluoro-4(pyridin-2-ylmethoxy)-phenyl]-[2-(S)-(2-(R)-methyl-pyrrolidin-1-ylmethyl)-pyrrolidin-1-yl]-methanone

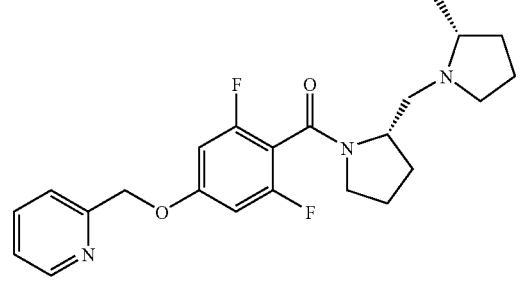

The title compound is prepared in a manner substantially analogous to Procedure F from 2,6-Difluoro-4-(pyridin-2-ylmethoxy)-benzoic acid methyl ester and 2-(R)-Methyl-1-(2-(S)-pyrrolidinylmethyl)pyrrolidine. MS (ES+) 416.2

EXAMPLE 51

[2-(S)-(2-(R)-Methyl-pyrrolidin-1-ylmethyl)-pyrrolidin-1-yl]-[4-(pyridin-2-ylmethoxy)-phenyl]-methanone

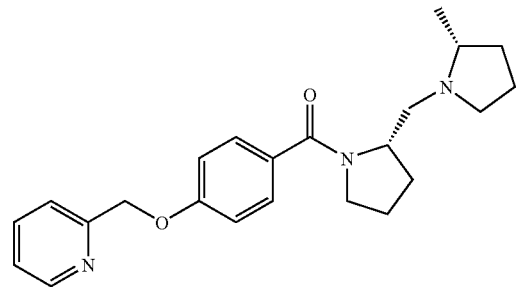

The title compound is prepared in a manner substantially analogous to Procedure F from 4-(Pyridin-2-ylmethoxy)-benzoic acid methyl ester and 2-(R)-Methyl-1-(2-(S)-pyrrolidinylmethyl)pyrrolidine. MS (ES+) 380.2

EXAMPLE 52

[4-(Pyridin-2-ylmethoxy)-phenyl]-(2-(R)-pyrrolidin-1-ylmethyl-pyrrolidin-1-yl)-methanone

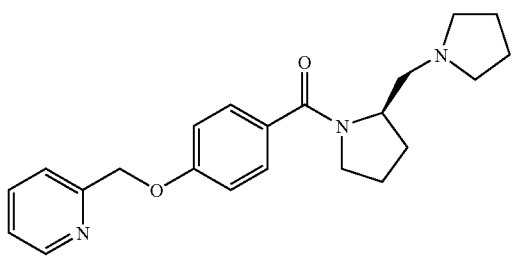

The title compound is prepared in a manner substantially analogous to Procedure F from 4-(Pyridin-2-ylmethoxy)-benzoic acid methyl ester and 1-[(2R)-2-pyrrolidinylmethyl]pyrrolidine [CAS 60419-23-0]. MS (ES+) 366.3

EXAMPLE 53

[2-Fluoro-4-(6-methyl-pyridin-2-ylmethoxy)-phenyl]-[2-(S)-(2-(R)-methyl-pyrrolidin-1-ylmethyl)-pyrrolidin-1-yl]-methanone

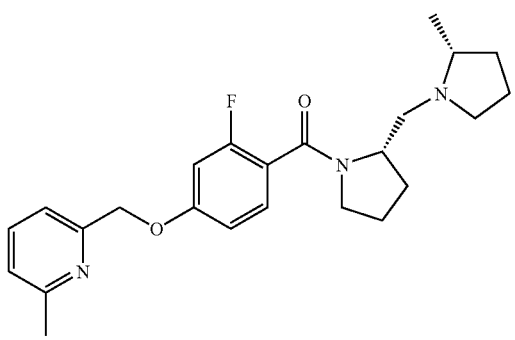

The title compound is prepared in a manner substantially analogous to Procedure F from 2-Fluoro-4-(6-methyl-pyridin-2-ylmethoxy)-benzoic acid methyl ester and 2-(R)-Methyl-1-(2-(S)-pyrrolidinylmethyl)pyrrolidine. MS (ES+) 412.3

EXAMPLE 54

[4-(6-Methyl-pyridin-2-ylmethoxy)-phenyl]-[2-(S)-(2-(R)-methyl-pyrrolidin-1-ylmethyl)-pyrrolidin-1-yl]-methanone

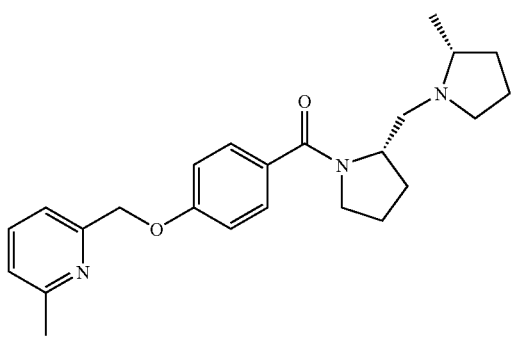

The title compound is prepared in a manner substantially analogous to Procedure F from 4-(6-Methyl-pyridin-2-ylmethoxy)-benzoic acid methyl ester and 2-(R)-Methyl-1-(2-(S)-pyrrolidinylmethyl)pyrrolidine. MS (ES+) 412.3

EXAMPLE 55

[2-Fluoro-4-(4-methanesulfonyl-benzyloxy)-phenyl]-[2-(S)-(2-(R)-methyl-pyrrolidin-1-ylmethyl)-pyrrolidin-1-yl]-methanone

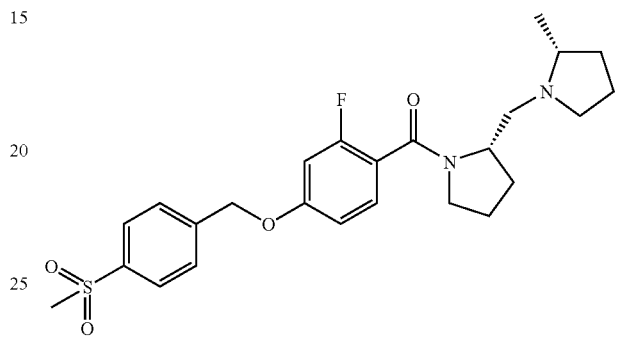

The title compound is prepared in a manner substantially analogous to Procedure F from 2-fluoro-4-(4-methanesulfonyl-benzyloxy)-benzoic acid methyl ester and 2-(R)-Methyl-1-(2-(S)-pyrrolidinylmethyl)pyrrolidine. MS (ES+) 475.2

EXAMPLE 56

[2-Fluoro-4-(4-fluoro-benzyloxy)-phenyl]-[2-(S)-(2-(R)-methyl-pyrrolidin-1-ylmethyl)-pyrrolidin-1-yl]-methanone trifluoroacetate salt

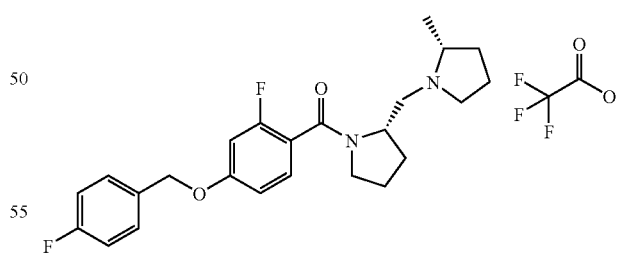

The title compound is prepared in a manner substantially analogous to Procedure B from (2-Fluoro-4-hydroxy-phenyl)-[2-(S)(2-(R)-methyl-pyrrolidin-1-ylmethyl)-pyrrolidin-1-yl]-methanone and 4-fluorobenzyl bromide. MS (ES+) 415.3

EXAMPLE 57

[4-(2-Benzenesulfonylmethyl-benzyloxy)-2-fluoro-phenyl]-[2-(S)-(2-(R)-methyl-pyrrolidin-1-ylmethyl)-pyrrolidin-1-yl]-methanone trifluoroacetate salt

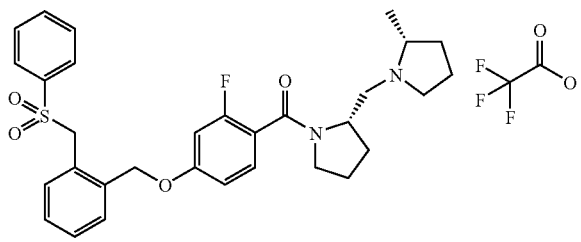

The title compound is prepared in a manner substantially analogous to Procedure B from (2-Fluoro-4-hydroxy-phenyl)-[2-(S)(2-(R)-methyl-pyrrolidin-1-ylmethyl)-pyrrolidin-1-yl]-methanone and 1-bromomethyl-2-[(phenylsulfonyl)methyl]benzene. MS (ES+) 551.2

EXAMPLE 58

[2-Fluoro-4-(6-methoxy-pyridin-3-ylmethoxy)-phenyl]-[2-(S)-(2-(R)-methyl-pyrrolidin-1-ylmethyl)-pyrrolidin-1-yl]-methanone trifluoroacetate salt

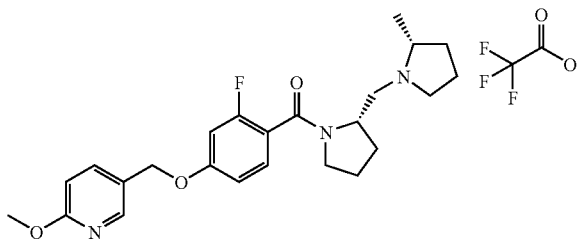

The title compound is prepared in a manner substantially analogous to Procedure B from (2-Fluoro-4-hydroxy-phenyl)-[2-(S)(2-(R)-methyl-pyrrolidin-1-ylmethyl)-pyrrolidin-1-yl]-methanone and 5-(chloromethyl)-2-methoxy-pyridine hydrochloride [CAS 120276-36-0]. MS (ES+) 428.3

EXAMPLE 59

[4-(2-Fluoro-4-trifluoromethanesulfonyl-benzyloxy)-phenyl]-[2-(S)-(2-(R)-methyl-pyrrolidin-1-ylmethyl)-pyrrolidin-1-yl]-methanone

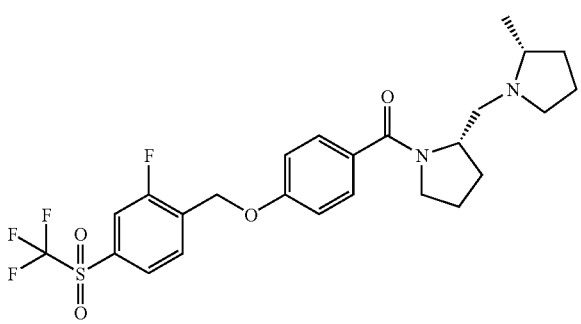

The title compound is prepared in a manner substantially analogous to Procedure F from 2-fluoro-4-(4-trifluoromethanesulfonyl-benzyloxy)-benzoic acid methyl ester and 2-(R)-Methyl-1-(2-(S)-pyrrolidinylmethyl)pyrrolidine. MS (ES+) 529.3

The optimal time for performing the reactions of the Schemes, Preparations, and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The compound of Formula I is preferably formulated in a unit dosage form prior to administration. Therefore, yet another embodiment of the present invention is a pharmaceutical composition comprising a compound of Formula I and one or more pharmaceutically acceptable carriers, diluents or excipients.

The present pharmaceutical compositions are prepared by known procedures using well-known and readily available ingredients. In making the formulations of the present invention, the active ingredient (Formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Utility

Compounds of Formula I are effective as antagonists or inverse agonists of the histamine H3 receptor, and thus inhibit the activity of the H3 receptor. More particularly, these compounds are selective antagonists or inverse agonists of the histamine H3 receptor. As selective antagonists or inverse agonists, the compounds of Formula I are useful in the treatment of diseases, disorders, or conditions responsive to the inactivation of the histamine H3 receptor, including but not limited to obesity and other eating-related disorders, and cognitive disorders. It is postulated that selective antagonists or inverse agonists of H3R will raise brain histamine levels and possibly that of other monoamines resulting in inhibition of food consumption while minimizing peripheral consequences. Although a number of H3R antagonists are known in the art, none have proven to be satisfactory obesity or cognitive drugs. There is increasing evidence that histamine plays an important role in energy homeostasis. Histamine, acting as a neurotransmitter in the hypothalamus, suppressed appetite. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor H4R has been recently identified. H4R is found in high levels in peripheral white blood cells; only low levels have been identified in the brain by some investigators while others cannot detect it in the brain. However, any drug discovery effort initiated around H3R must consider H4R as well as the other subtypes.

The compounds of the present invention can readily be evaluated by using a competitive inhibition Scintillation Proximity Assay (SPA) based on a H3R binding assay using [3H] α methylhistamine as ligand. Stable cell lines, including but not limited to HEK can be transfected with cDNA coding for H3R to prepare membranes used for the binding assay. The technique is illustrated below (Preparation of Histamine Receptor Subtype Membranes) for the histamine receptor subtypes.

Membranes isolated as described in (Preparation of Histamine Receptor Subtype Membranes) were used in a [35S] GTP$_\gamma$S functional assay. Binding of [35S]GTP$_\gamma$S to membranes indicates agonist activity. Compounds of the invention of Formula I were tested for their ability to inhibit binding in the presence of agonists. Alternately, the same transfected cell lines were used for a cAMP assay wherein H3R agonists inhibited forskolin-activated synthesis of cAMP. Compounds of Formula I were tested for their ability to permit forskolin-stimulated cAMP synthesis in the presence of agonist.

Preparation of Histamine Receptor Subtype Membranes

A. Preparation H1R Membranes cDNA for the human histamine 1 receptor (H1R) was cloned into a mammalian expression vector containing the CMV promoter (pcDNA3.1(+), Invitogen) and transfected into HEK293 cells using the FuGENE Tranfection Reagent (Roche Diagnostics Corporation). Transfected cells were selected using G418 (500 µ/ml). Colonies that survived selection were grown and tested for histamine binding to cells grown in 96-well dishes using a scintillation proximity assay (SPA) based radioligand binding assay. Briefly, cells, representing individual selected clones, were grown as confluent monolayers in 96-well dishes (Costar Clear Bottom Plates, #3632) by seeding wells with 25,000 cells and growing for 48 hours (37° C., 5% $CO_2$). Growth media was removed and wells were rinsed two times with PBS (minus $Ca^{2+}$ or $Mg^{2+}$). For total binding, cells were assayed in a SPA reaction containing 50 mM Tris-HCL (assay buffer), pH 7.6, 1 mg wheat germ agglutinin SPA beads (Amersham Pharmacia Biotech, #RPNQ0001), and 0.8 nM $^3$H-pyrilamine (Net-594, NEN) (total volume per well=200 µl). Astemizole (10 µM, Sigma #A6424) was added to appropriate wells to determine nonspecific binding. Plates were covered with FasCal and incubated at room temperature for 120 minutes. Following incubation, plates were centrifuged at 1,000 rpm (~800 g) for 10 minutes at room temperature. Plates were counted in a Wallac Trilux 1450 Microbeta scintillation counter. Several clones were selected as positive for binding, and a single clone (H1R40) was used to prepare membranes for binding studies. Cell pellets, representing ~10 grams, were resuspended in 30 ml assay buffer, mixed by vortexing, and centrifuged (40,000 g at 4° C.) for 10 minutes. The pellet resuspension, vortexing, and centrifugation was repeated 2 more times. The final cell pellet was resuspended in 30 ml and homogenized with a Polytron Tissue Homogenizer. Protein determinations were done using the Coomassie Plus Protein Assay Reagent (Pierce). Five micrograms of protein was used per well in the SPA receptor-binding assay.

B. Preparation of H2R Membranes cDNA for the human histamine 2 receptor was cloned, expressed and transfected into HEK 293 cells as described above. Histamine binding to cells was assayed by SPA described above. For total binding, cells were assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 µl). Cimetidine (10 µM, Sigma #C4522) was added to appropriate wells to determine non-specific binding.

Several clones were selected as positive for binding, and a single clone (H2R10) was used to prepare membranes for binding studies. Five micrograms of protein was used per well in the SPA receptor-binding assay.

C. Preparation of H3R Membranes cDNA for the human histamine 3 receptor was cloned and expressed as described in (A. Preparation H1R membranes), above. Transfected cells were selected using G418 (500 µ/ml), grown, and tested for histamine binding by the SPA described above. For total binding, cells were assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM ($^3$H)-n-alpha-methylhistamine (NEN, NET1027) (total volume per well=200 µl). Thioperimide was added to determine non-specific binding. Several clones were selected as positive for binding, and a single clone (H3R8) was used to prepare membranes for binding studies described above. Five micrograms of protein was used per well in the SPA receptor-binding assay.

The compounds according to the invention preferably have a Ki value of no greater than 5 µM as determined by the Histamine H3 Receptor Binding Assay disclosed herein. All compounds set forth in the examples exhibit affinity for the H3 receptor greater than 1 uM. More preferably, the compounds according to the invention have a Ki value of less than 1 µM, preferably of less than 500 nM and even more preferred of less than 200 nM as determined by the Histamine H3 Receptor Binding Assay disclosed herein. Most preferred compounds of the invention exhibit affinity for the H3 receptor greater than 20 nM. Furthermore, the compounds according to the invention preferably have a higher binding affinity to the histamine H3 receptor than to the H4R receptor.

D. Preparation of H4R Membranes cDNA for the human H4R receptor was cloned and expressed as described in (A. Preparation H1R membranes), above. Transfected cells were selected, tested for histamine binding, and selected. HEK293 GPRv53 50 cells were grown to confluency in DMEM/F12 (Gibco) supplemented with 5% FBS and 500 ug/ml G418 and washed with Delbecco's PBS (Gibco) and harvested by scraping. Whole cells were homogenized with a Polytron tissuemizer in binding buffer, 50 mM Tris pH 7.5. Cell lysates, 50 ug, were incubated in 96 well dishes with 3 nM (3H) Histamine and compounds in binding buffer for 2 hours at room temperature. Lysates were filtered through glass fiber filters (Perkin Elmer) with a Tomtec cell harvester. Filters were counted with melt-on scintillator sheets (Perkin Elmer) in a Wallac Trilux 1450 Microbeta Scintillation counter for 5 minutes.

Pharmacological Results cAMP ELISA

HEK293H3R8 cells prepared as described above were seeded at a density of 50,000 cells/well and grown overnight in DMEM/F12 (Gibco) supplemented with 5% FBS and 500 ug/ml G418. The next day tissue culture medium was removed and replaced with 50 µl cell culture medium containing 4 mM 3-isobutyl-1-methylxanthine (Sigma) and incubated for 20 minutes at room temperature. Antagonist were added in 50 µl cell culture medium and incubated for 20 minutes at room temperature. Agonist R (−)α methylhistamine (RBI) at a dose response from $1\times10^{-10}$ to $1\times10^{-5}$ M was then added to the wells in 50 µl cell culture medium and incubated for 5 minutes at room temperature. Then 50 µl of cell culture medium containing 20 µM Forskolin (Sigma) was added to each well and incubated for 20 minutes at room temperature. Tissue culture medium was removed and cells were lysed in 0.1M HCl and cAMP was measured by ELISA (Assay Designs, Inc.).

[35S] GTP γ [S] Binding Assay

Antagonist activity of selected compounds was tested for inhibition of [35S] GTP γ [S] binding to H3R membranes in the presence of agonists. Assays were run at room temperature in 20 mM HEPES, 100 mM NaCl, 5 mM MgCl$_2$ and 10 uM GDP at pH 7.4 in a final volume of 200 ul in 96-well Costar plates. Membranes isolated from H3R8-expressing HEK293 cell line (20 ug/well) and GDP were added to each well in a volume of 50 µl assay buffer. Antagonist was then added to the wells in a volume of 50 µl assay buffer and incubated for 15 minutes at room temperature. Agonist R(−) alpha methylhistamine (RBI) at either a dose response from $1\times10^{-10}$ to $1\times10^{-5}$ M or fixed concentration of 100 nM were then added to the wells in a volume of 50 µl assay buffer and incubated for 5 minutes at room temperature. GTP γ [35S] was added to each well in a volume of 50 µl assay buffer at a final concentration of 200 pM, followed by the addition of 50 µl of 20 mg/ml WGA coated SPA beads (Amersham). Plates were counted in Wallac Trilux 1450 Microbeta scintillation counter for 1 minute. Compounds that inhibited more than 50% of the specific binding of radioactive ligand to the receptor were serially diluted to determine a K[i](nM). The results are given below for the indicated compound.

TABLE 2

| Example | Ki (nM) |
|---|---|
| 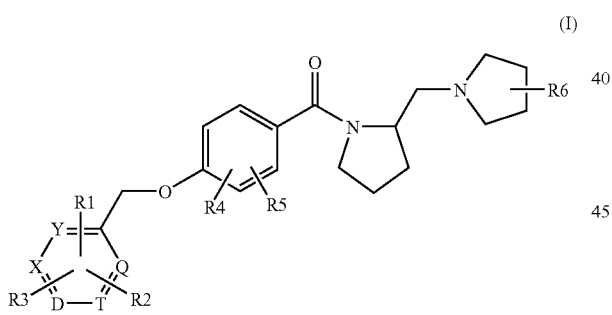 | 19 |
| | 4.1 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed:

1. A compound structurally represented by Formula I (I)

or a pharmaceutically acceptable salt thereof wherein:

Q, T, D, X, and Y independently represent carbon (substituted with hydrogen or the optional substitutents indicated herein) or nitrogen, provided that no more than two of Q, T, D, X, and Y are nitrogen;

R1, R2, and R3 are independently at each occurrence
—H, -halogen, -($C_1$-$C_7$) alkyl (optionally substituted with one to three halogens), —$CF_3$, —CN, —C(O)R10, —CO(O)R7, —CO(O)Li, —C(O)($C_3$-$C_5$)cycloalkyl, —C(O)NR7R8, —$OCF_3$, —OR7, —NR7R8, —NR9$SO_2$R7, —NR9C(O)R7, —NR9$CO_2$R7, —NR9C(O)NR7R8, —SR7, —$SO_2$R7, —$SO_2CF_3$, —$SO_2$NR7R8, —S(O)R7, —$CH_2SO_2$R10, or -heteroaryl-R9; provided that when D is nitrogen, then R1 or R2 or R3 are not attached to D, and provided that when X is nitrogen, then R1 or R2 or R3 are not attached to X, and provided that when T is nitrogen, then R1 or R2 or R3 are not attached to T, and provided that when Q is nitrogen, then R1 or R2 or R3 are not attached to Q, and provided that when Y is nitrogen, then R1 or R2 or R3 are not attached to Y;

R4 and R5 are independently at each occurrence
—H, —OH, -halogen, —$CF_2$H, —$CF_3$, -($C_1$-$C_3$)alkyl (optionally substituted with one to three halogens), or —OR9;

R6 is
—H, -halogen, —$CF_3$, -($C_1$-$C_3$)alkyl (optionally substituted with one to three halogens), —$NH_2$, —NR7R8, —OH, or —OR7;

R7 and R8 are independently at each occurrence
—H or -($C_1$-$C_7$) alkyl (optionally substituted with one to three halogens), wherein R7 and R8 can combine with the atom to which they are attached to form a three to seven membered ring;

R9 is —H or -($C_1$-$C_3$) alkyl (optionally substituted with one to three halogens); and R10 is —H, -($C_1$-$C_7$)alkyl (optionally substituted with one to three halogens), or -phenyl.

2. The compound or salt of claim 1, wherein D, X, Q, Y, and T are carbon (substituted with hydrogen or the optional substituents indicated herein).

3. The compound or salt of claim 1, wherein one of D, X, Q, Y or T is nitrogen.

4. The compound or salt of claim 1 wherein two of D, X, Q, Y or T are nitrogen.

5. The compound or salt of claim 1 wherein D is carbon and R1 is attached to D.

6. The compound or salt of claim 5 wherein R4 is halogen.

7. The compound or salt of claim 6 wherein R6 is -$CH_3$.

8. A compound or salt of claim 2 wherein R1 is -halogen, -($C_1$-$C_7$) alkyl(optionally substituted with one to three halogens), —CN, —C(O)R10, —CO(O)Li, —C(O)($C_3$-$C_5$)cycloalkyl, —C(O)NR7R8, —$OCF_3$, —OR7, —NR7R8, —NR9$SO_2$R7, —NR9C(O)R7, —NR9$CO_2$R7, —NR9C(O)NR7R8, —SR7, —$SO_2$R7, —$SO_2CF_3$, —$SO_2$ NR7R8, —S(O)R7, —$CH_2$ $SO_2$NR10, or -heteroaryl-R9, and R2 and R3 are independently at each occurrence -H, -halogen, -($C_1$-$C_7$) alkyl(optionally substituted with one to three halogens), —CN, —C(O)R7, —C(O)($C_3$-$C_5$)cycloalkyl, —C(O)NR7R8, —$OCF_3$, —OR7, —NR7R8, —$NR9SO_2$ R7, —NR9C(O)R7, —$NR9CO_2R7$, —NR9C(O)NR7R8, —SR7, —$SO_2R7$, —$SO_2CF_3$, —$SO_2NR7R8$, —S(O)R7, —$CH_2SO_2NR10$, or -heteroaryl-R9, and R4 and R5 are independently —H, —OH, -halogen, —$CF_2H$, —$CF_3$, -($C_1$-$C_3$) alkyl (optionally substituted with one to three halogens), or -OR9, provided that when R4 is —H, then R5 is not —H.

9. A compound or salt of claim 1 wherein Q is carbon (substituted with hydrogen or the optional substituents indicated herein) or nitrogen; D is carbon (substituted with hydrogen or the optional substituents indicated herein) or nitrogen; T is carbon (substituted with hydrogen or the optional substituents indicated herein) or nitrogen; X is carbon (substituted with hydrogen or the optional substituents indicated herein) or nitrogen; R1 is hydrogen, —CN, —$SCF_3$, —$OCF_3$, —$OCH_3$, —$CF_3$, methyl, —$CH_2$—$S(O)_2$-phenyl, —C(O)-phenyl, fluoro, chloro, —$S(O)_2$—$CH_3$, —$S(O)_2$—CF3, —$C(O)N(CH_2)_2$, —$C(O)NHCH_2$, —$C(O)OCH_3$, —C(O)OLi, —C(O)-pyrrolidinyl, —C(O)-azetidinyl, or —C(O)-piperidinyl; R2 is hydrogen or fluoro; R3 is hydrogen; R4 is hydrogen or fluoro;

R5 is hydrogen or fluoro; and R6 is hydrogen or methyl.

10. The compound of claim 1 selected from the group consisting of formulae X1 to X57:

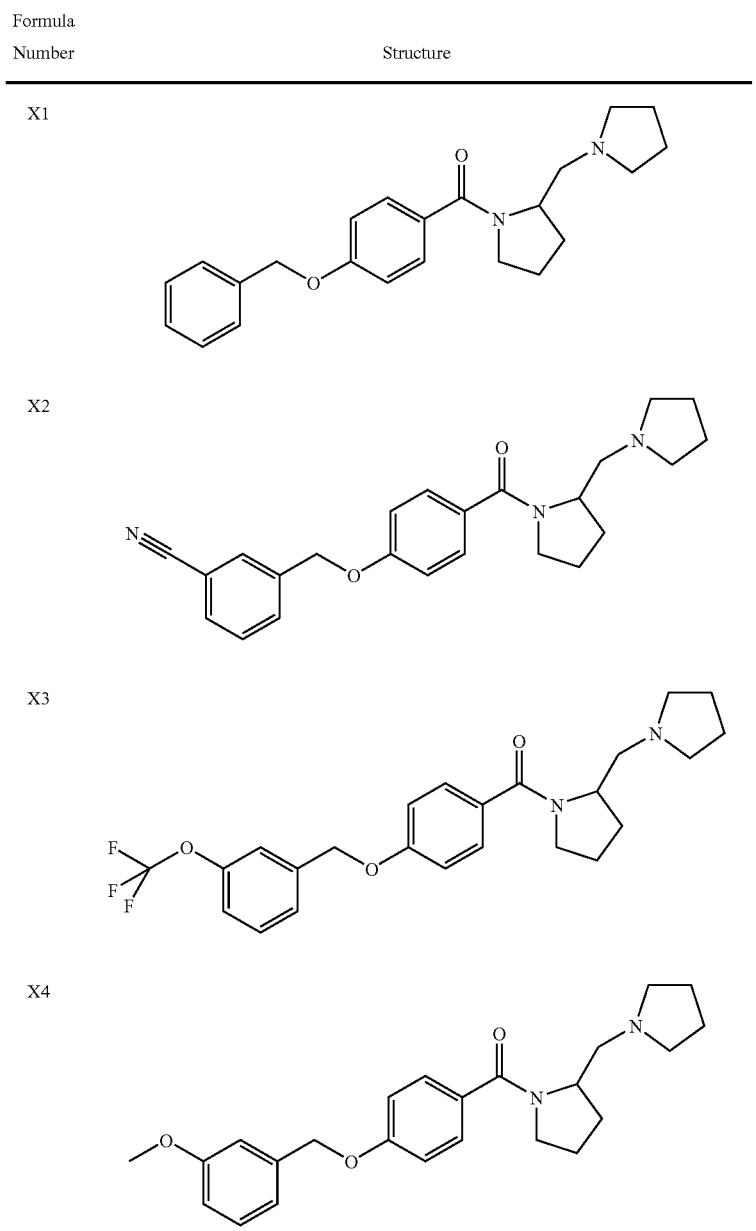

| Formula Number | Structure |
|---|---|
| X1 | 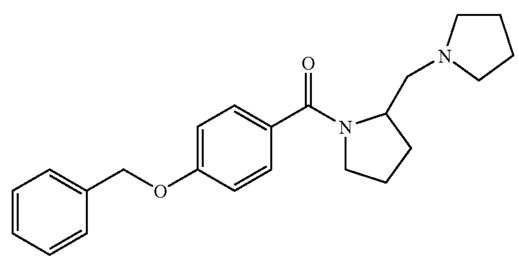 |
| X2 | 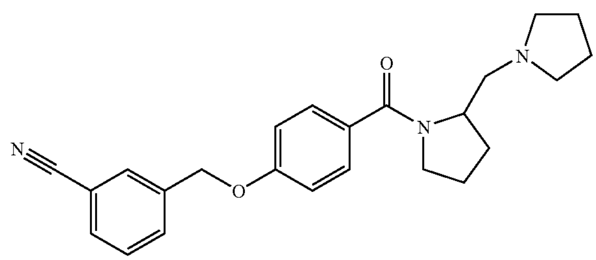 |
| X3 | 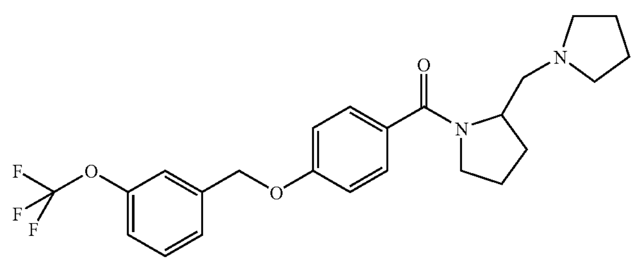 |
| X4 | 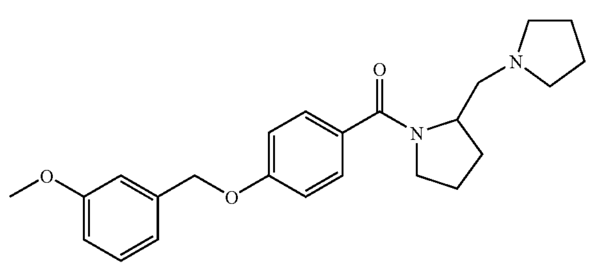 |

-continued

| Formula Number | Structure |
|---|---|
| X5 | 3-(trifluoromethyl)benzyl 4-((2-(pyrrolidin-1-ylmethyl)pyrrolidin-1-yl)carbonyl)phenyl ether |
| X6 | 4-(trifluoromethyl)benzyl 4-((2-(pyrrolidin-1-ylmethyl)pyrrolidin-1-yl)carbonyl)phenyl ether |
| X7 | 4-methylbenzyl 4-((2-(pyrrolidin-1-ylmethyl)pyrrolidin-1-yl)carbonyl)phenyl ether |
| X8 | 3-methylbenzyl 4-((2-(pyrrolidin-1-ylmethyl)pyrrolidin-1-yl)carbonyl)phenyl ether |
| X9 | 4-cyanobenzyl 4-((2-(pyrrolidin-1-ylmethyl)pyrrolidin-1-yl)carbonyl)phenyl ether |

-continued

| Formula Number | Structure |
|---|---|
| X10 | 4-(trifluoromethoxy)benzyl 4-((2-(pyrrolidin-1-ylmethyl)pyrrolidin-1-yl)carbonyl)phenyl ether |
| X11 | 3-fluorobenzyl 4-((2-(pyrrolidin-1-ylmethyl)pyrrolidin-1-yl)carbonyl)phenyl ether |
| X12 | 4-fluorobenzyl 4-((2-(pyrrolidin-1-ylmethyl)pyrrolidin-1-yl)carbonyl)phenyl ether |
| X13 | 2-methylbenzyl 4-((2-(pyrrolidin-1-ylmethyl)pyrrolidin-1-yl)carbonyl)phenyl ether |
| X14 | 2,6-difluorobenzyl 4-((2-(pyrrolidin-1-ylmethyl)pyrrolidin-1-yl)carbonyl)phenyl ether |
| X15 | 2-(trifluoromethyl)benzyl 4-((2-(pyrrolidin-1-ylmethyl)pyrrolidin-1-yl)carbonyl)phenyl ether |

-continued
| Formula Number | Structure |
| --- | --- |
| X16 | 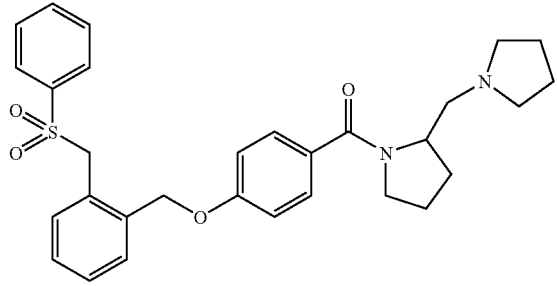 |
| X17 | 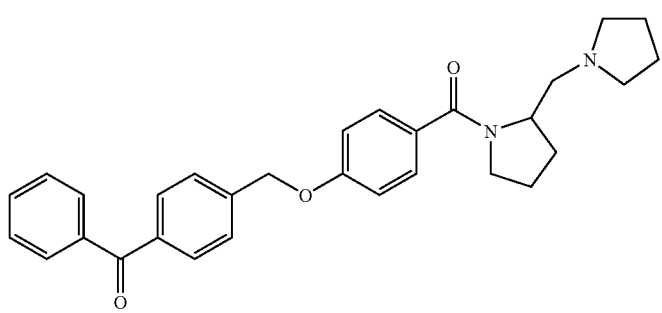 |
| X18 | 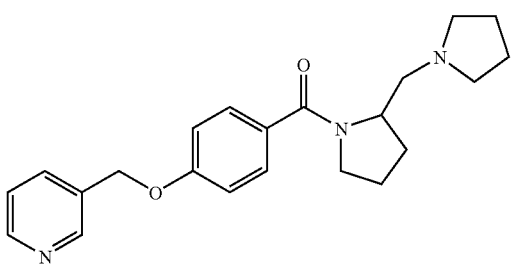 |
| X19 | 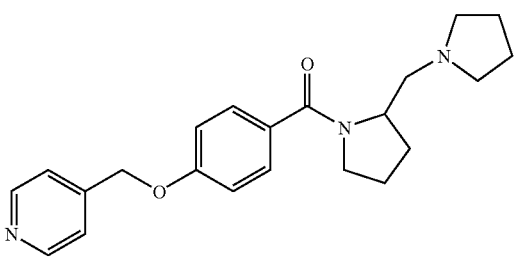 |
| X20 | 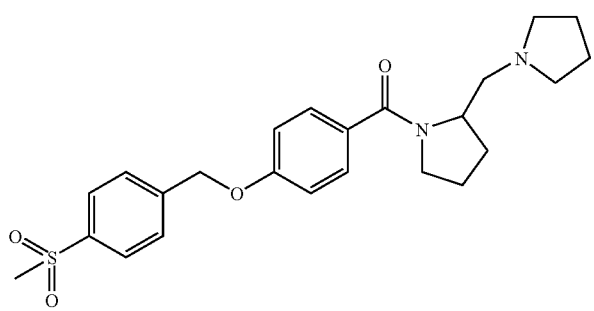 |

-continued
| Formula Number | Structure |
|---|---|
| X21 | 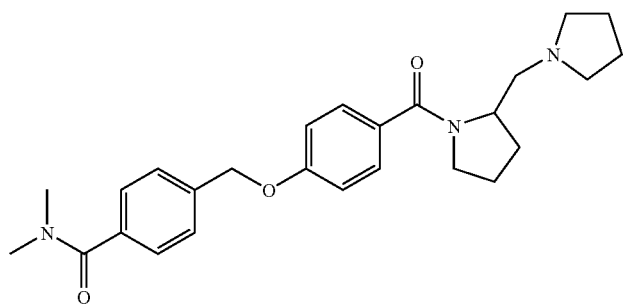 |
| X22 | 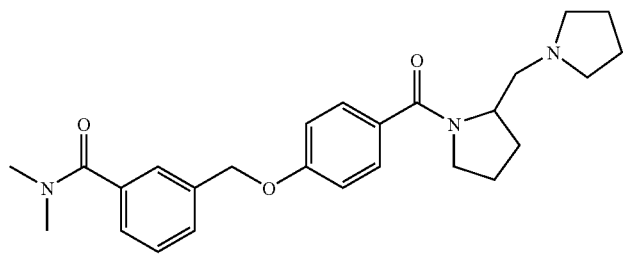 |
| X23 | 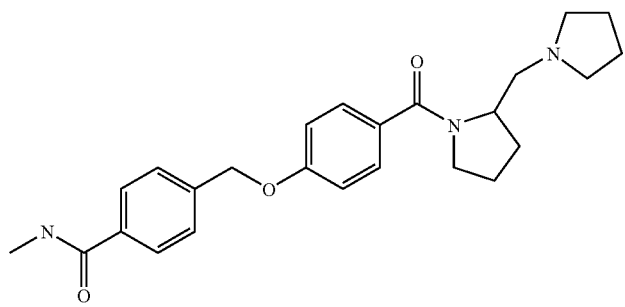 |
| X24 | 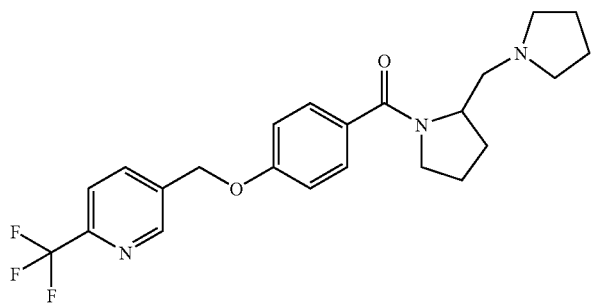 |
| X25 | 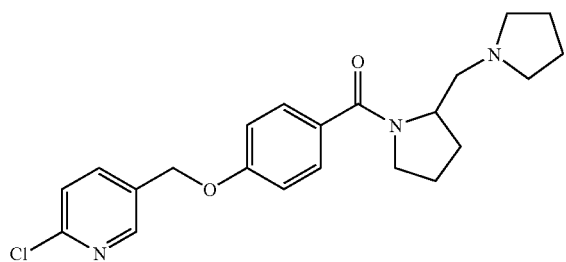 |

-continued

| Formula Number | Structure |
|---|---|
| X26 | 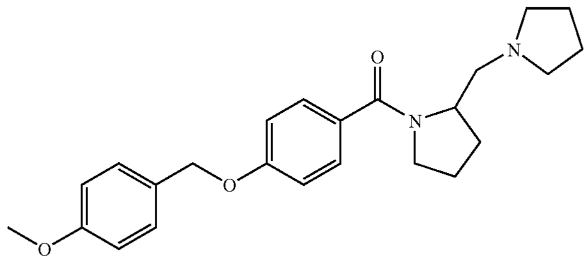 |
| X27 | 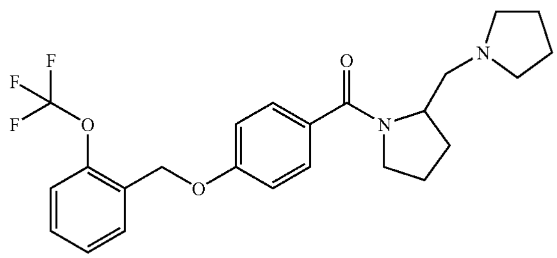 |
| X28 | 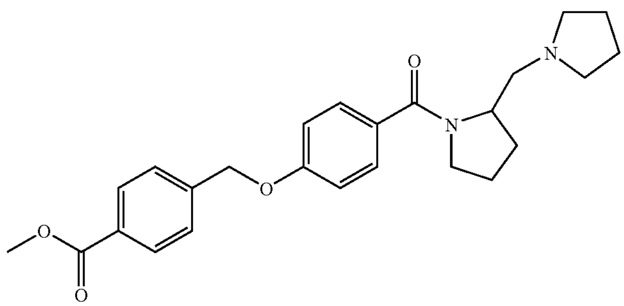 |
| X29 | 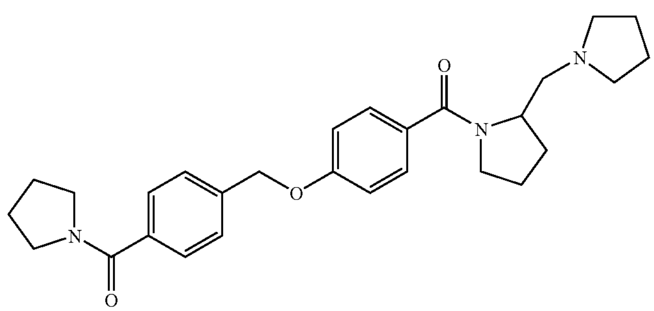 |
| X30 | 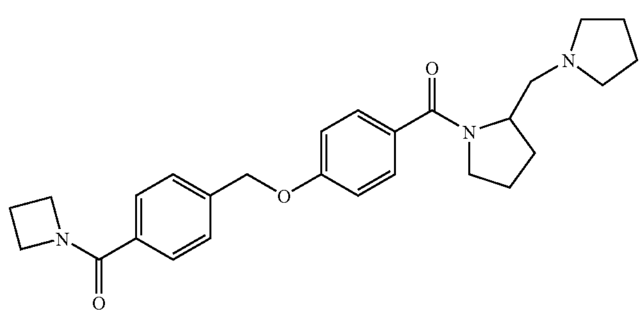 |

-continued
| Formula Number | Structure |
|---|---|
| X31 | 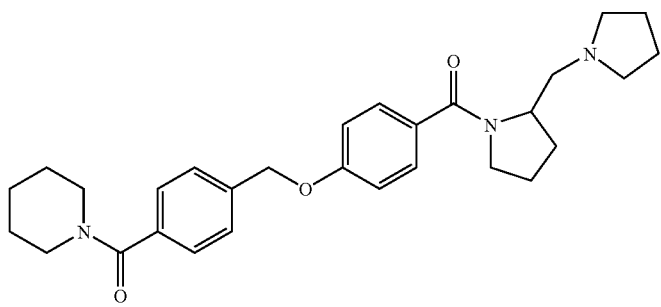 |
| X32 | 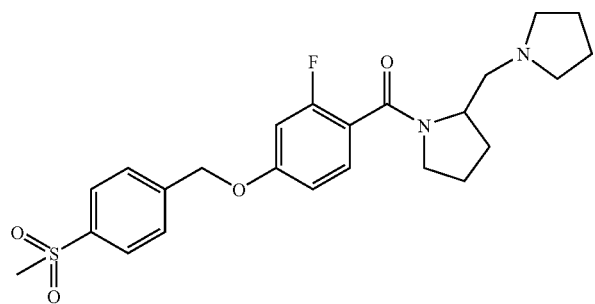 |
| X33 | 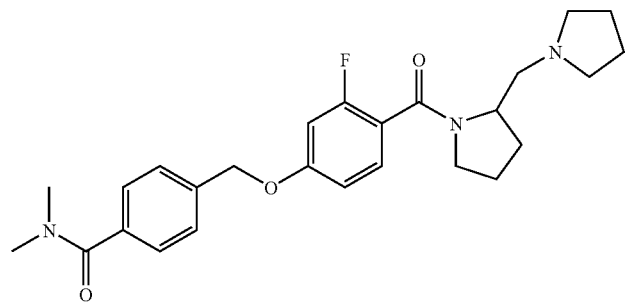 |
| X34 | 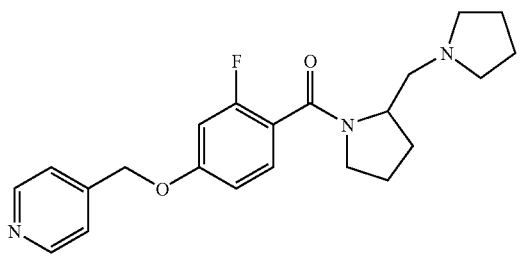 |
| X35 | 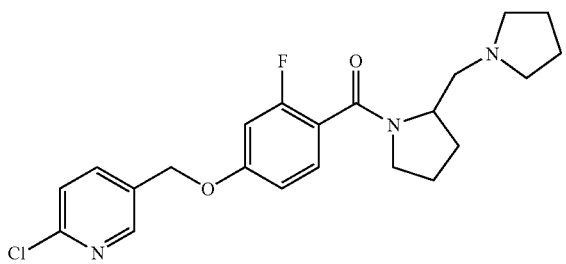 |

-continued
| Formula Number | Structure |
|---|---|
| X36 | 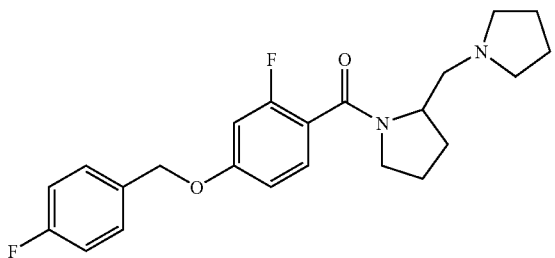 |
| X37 | 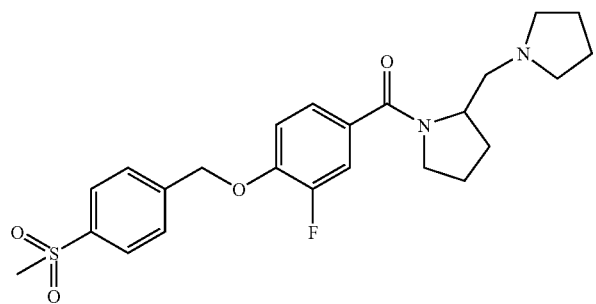 |
| X38 | 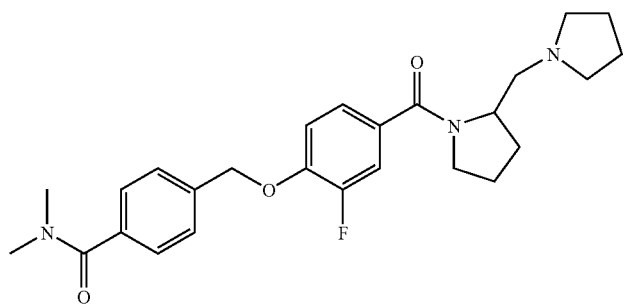 |
| X39 | 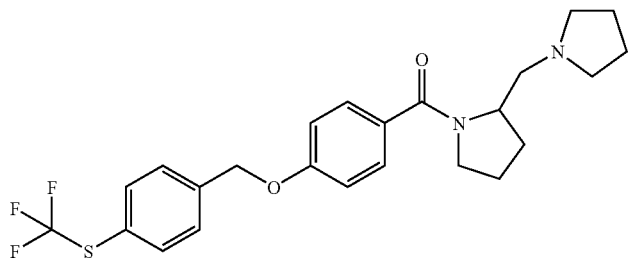 |
| X40 | 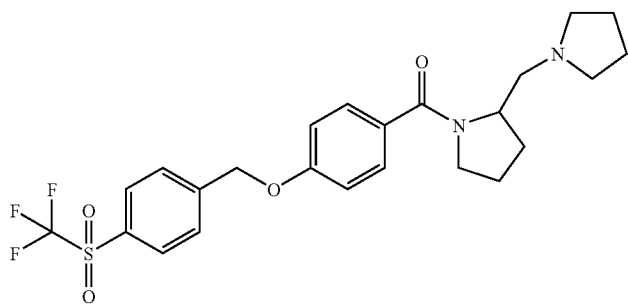 |

-continued

| Formula Number | Structure |
|---|---|
| X41 | (4-(pyridin-2-ylmethoxy)phenyl)(2-(pyrrolidin-1-ylmethyl)pyrrolidin-1-yl)methanone |
| X42 | (4-((4-fluorobenzyl)oxy)phenyl)(2-(pyrrolidin-1-ylmethyl)pyrrolidin-1-yl)methanone |
| X43 | (2-fluoro-4-(pyridin-2-ylmethoxy)phenyl)(2-(pyrrolidin-1-ylmethyl)pyrrolidin-1-yl)methanone |
| X44 | (3-fluoro-4-(pyridin-2-ylmethoxy)phenyl)(2-(pyrrolidin-1-ylmethyl)pyrrolidin-1-yl)methanone |
| X45 | (2,6-difluoro-4-(pyridin-2-ylmethoxy)phenyl)(2-(pyrrolidin-1-ylmethyl)pyrrolidin-1-yl)methanone |

| Formula Number | Structure |
|---|---|
| X46 | 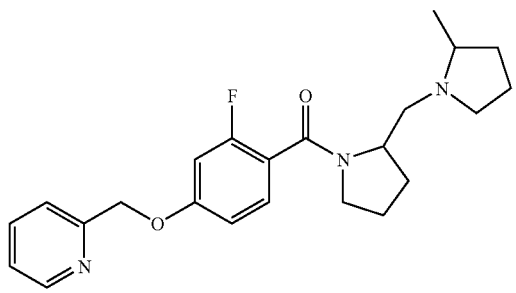 |
| X47 | 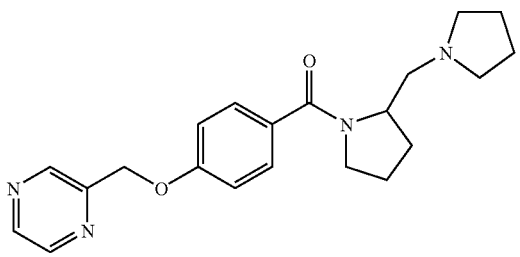 |
| X48 | 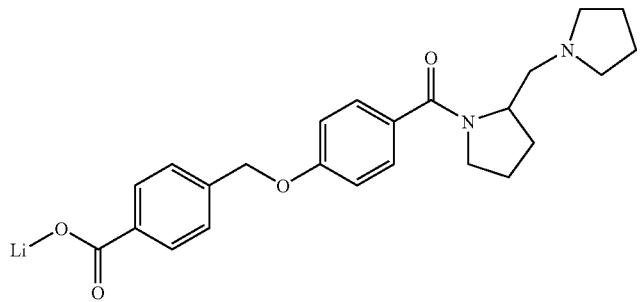 |
| X49 | 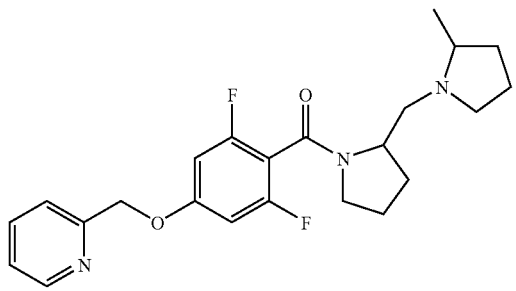 |
| X50 | 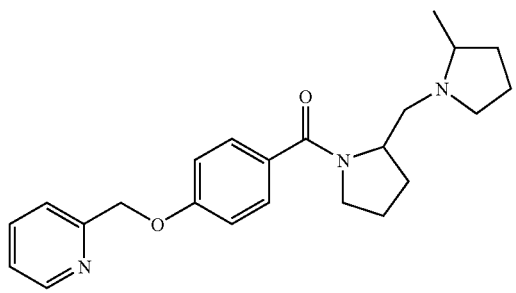 |

-continued
| Formula Number | Structure |
|---|---|
| X51 | 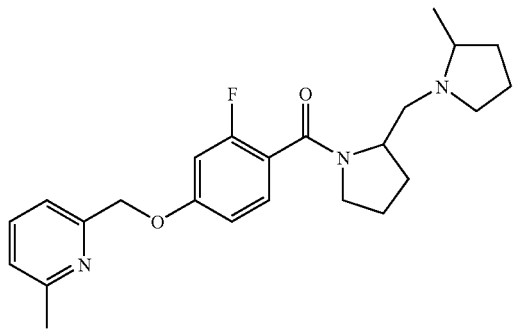 |
| X52 | 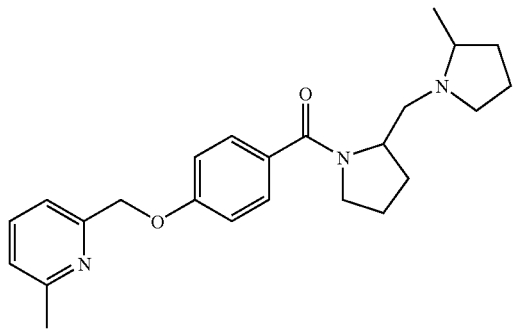 |
| X53 | 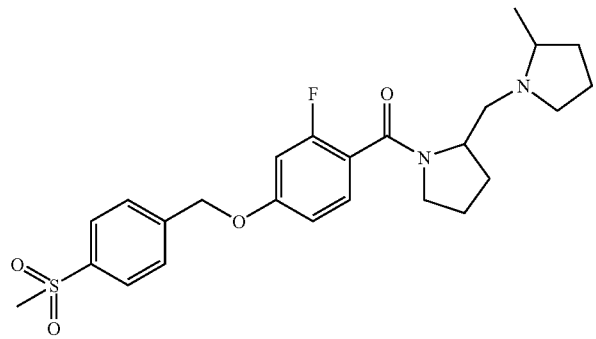 |
| X54 | 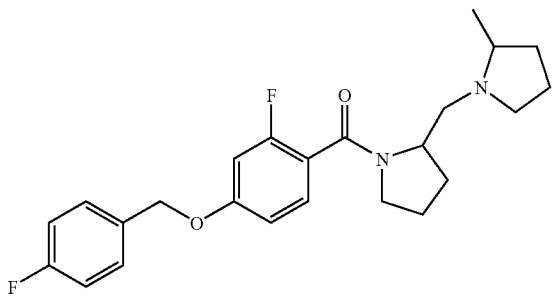 |

| Formula Number | Structure |
|---|---|
| X55 | 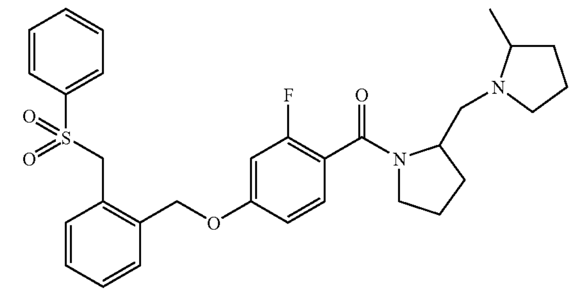 |
| X56 | 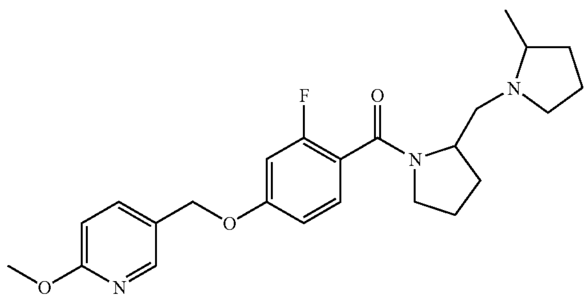 |
| X57 | | or a pharmaceutically acceptable salt thereof.

11. The compound of claim 1, selected from the group consisting of:
(4-Benzyloxy-phenyl)-(2-(S)-pyrrolidin-1-ylmethyl-pyrrolidin-1-yl)- methanone,
3-[4-(2-(S)-pyrrolidin-1-ylmethyl-pyrrolidine-1-carbonyl)-phenoxymethyl]-benzomtrile,
(2-(S)-pyrrolidin-1-ylmethyl-pyrrolidin-1-yl)-[4-(3-trifluoromethoxy-benzyloxy) -phenyl]-methanone,
[4-(3-Methoxy-benzyloxy)-phenyl]-(2-(S)-pyrrolidin-1-ylmethyl-pyrrolidin-1-yl) -methanone,
(2-(S)-pyrrolidin-1-ylmethyl-pyrrolidin-1-yl)-[4-(3-trifluoromethyl-benzyloxy)-phenyl]-methanone,
(2-(S)-pyrrolidin-1-ylmethyl-pyrrolidin-1-yl)-[4-(4-trifluoromethyl-benzyloxy)-phenyl]-methanone,
4-(4-Methyl-benzyloxy)-phenyl]-(2-(S)-pyrrolidin-1-ylmethyl-pyrrolidin-1-yl) -methanone,
[4-(3-Methyl-benzyloxy)-phenyl]-(2-(S)-pyrrolidin-1-ylmethyl-pyrrolidin-1-yl) -methanone,
4-[4-(2-(S)-pyrrolidin-1-ylmethyl-pyrrolidine-1-carbonyl)-phenoxymethyl]-benzonitrile,
(2-(S)-pyrrolidin-1-ylmethyl-pyrrolidin-1-yl)-[4-(4-trifluoromethoxy-benzyloxy) -phenyl]-methanone,
[4-(3-Fluoro-benzyloxy)-phenyl]-(2-(S)-pyrrolidin-1-ylmethyl-pyrrolidin-1-yl) -methanone,
[4-(4-Fluoro-benzyloxy)-phenyl]-(2-(S)-pyrrolidin-1-ylmethyl-pyrrolidin-1-yl) -methanone,
[4-(2-Methyl-benzyloxy)-phenyl]-(2-(S)-pyrrolidin-1-ylmethyl-pyrrolidin-1-yl) -methanone,
[4-(2,6-Difluoro-benzyloxy)-phenyl]-(2-(S)-pyrrolidin-1-ylmethyl-pyrrolidin-1-yl) -methanone,
(2-(S)-pyrrolidin-1-ylmethyl-pyrrolidin-1-yl)-[4-(2-trifluoromethyl-benzyloxy) -phenyl]-methanone,
[4-(2-Benzenesulfonylmethyl-benzyloxy)-phenyl]-(2-(S)-pyrrolidin-1-ylmethyl -pyrrolidin-1-yl)-methanone,
[4-(4-Benzoyl-benzyloxy)-phenyl]-(2-(S)-pyrrolidin-1-ylmethyl-pyrrolidin-l-yl) -methanone,
[4-(Pyridin-3-ylmethoxy)-phenyl]-(2-(S)-pyrrolidin-1-ylmethyl-pyrrolidin-l-yl) -methanone,
[4-(Pyridin-4-ylmethoxy)-phenyl]-(2-(S)-pyrrolidin-1-ylmethyl-pyrrolidin-l-yl) -methanone,
[4-(4-Methanesulfonyl-benzyloxy)-phenyl]-(2-(S)-pyrrolidin-1-ylmethyl -pyrrolidin-1-yl)-methanone,
N,N-Dimethyl-4-[4-(2-(S)-pyrrolidin-1-ylmethyl-pyrrolidine-1-carbonyl) -phenoxymethyl]-benzamide, N,N-Dimethyl-3-[4-(2-(S)-pyrrolidin-1-ylmethyl-pyrrolidine-1-carbonyl) -phenoxymethyl]-benzamide,
N-Methyl-4-[4-(2-(S)-pyrrolidin-1-ylmethyl-pyrrolidine-1-carbonyl) -phenoxymethyl]-benzamide,
(2-(S)-Pyrrolidin-1-ylmethyl-pyrrolidin-1-yl)-[4-(6-trifluoromethyl-pyridin-3 -ylmethoxy)-phenyl]-methanone,
[4-(6-Chloro-pyridin-3-ylmethoxy)-phenyl]-(2-(S)-pyrrolidin-1-ylmethyl -yrrolidin-1-yl)-methanone,
[4-(4-Methoxy-benzyloxy)-phenyl]-(2-(S)-pyrrolidin-1-ylmethyl-pyrrolidin-l-yl) -methanone,
(2-(S)-Pyrrolidin-1-ylmethyl-pyrrolidin-1-yl)-[4-(2-trifluoromethoxy-benzyloxy) -phenyl]-methanone,
4-[4-(2-(S)-Pyrrolidin-1-ylmethyl-pyrrolidine-1-carbonyl)-phenoxymethyl]-benzoic acid methyl ester,
{4-[4-(Pyrrolidine-1-carbonyl)-benzyloxy]-phenyl}-(2-(S)-pyrrolidin-1-ylmethyl -pyrrolidin-1-yl)-methanone,
{4-[4-(Azetidine-1-carbonyl)-benzyloxy]-phenyl}-(2-(S)-pyrrolidin-1-ylmethyl -pyrrolidin-1-yl)-methanone,
{4-[4-(Piperidine-1-carbonyl)-benzyloxy]-phenyl}-(2-(S)-pyrrolidin-1-ylmethyl -pyrrolidin-1-yl)-methanone,
[2-Fluoro-4-(4-methanesulfonyl-benzyloxy)-phenyl]-(2-(S)-pyrrolidin-1-ylmethyl -pyrrolidin-1-yl)-methanone,
4-[3-Fluoro-4-(2-(S)-pyrrolidin-1-ylmethyl-pyrrolidine-1-carbonyl) -phenoxymethyl]-N,N-dimethyl-benzamide,
[2-Fluoro-4-(pyridin-4-ylmethoxy)-phenyl]-(2-(S)-pyrrolidin-1-ylmethyl -pyrrolidin-1-yl)-methanone,
[4-(6-Chloro-pyridin-3-ylmethoxy)-2-fluoro-phenyl]-(2-(S)-pyrrolidin-1-ylmethyl -pyrrolidin-1-yl)-methanone,
[2-Fluoro-4-(4-fluoro-benzyloxy)-phenyl]-(2-(S)-pyrrolidin-1-ylmethyl-pyrrolidin -1-yl)-methanone,
[3-Fluoro4-(4-methanesulfonyl-benzyloxy)-phenyl]-(2-(S)-pyrrolidin-1-ylmethyl -pyrrolidin-1-yl)-methanone,
4-[2-Fluoro-4-(2-(S)-pyrrolidin-1-ylmethyl-pyrrolidine-1-carbonyl) -phenoxymethyl]-N,N-dimethyl-benzamide,
(2-(S)-Pyrrolidin-1-ylmethyl-pyrrolidin-1-yl)-[4-(4-trifluoromethylsulfanyl-benzyloxy) -phenyl]-methanone,
(2-(S)-Pyrrolidin-1-ylmethyl-pyrrolidin-1-yl)-[4-(4-trifluoromethanesulfonyl-benzyloxy) -phenyl]-methanone,
[4-(Pyridin-2-ylmethoxy)-phenyl]-(2-(S)-pyrrolidin-1-ylmethyl-pyrrolidin-l-yl) -methanone,
[4-(Pyridin-2-ylmethoxy)-phenyl]-(2-(S)-pyrrolidin-1-ylmethyl-pyrrolidin-l-yl) -methanone,
[4-(4-Fluoro-benzyloxy)-phenyl]-(2-(S)-pyrrolidin-1-ylmethyl-pyrrolidin-l-yl) -methanone,
[2-Fluoro-4-(pyridin-2-ylmethoxy)-phenyl]-(2-(S)-pyrrolidin-1-ylmethyl -pyrrolidin-1-yl)-methanone,
[2-Fluoro-4-(pyridin-2-ylmethoxy)-phenyl]-(2-(S)-pyrrolidin-1-ylmethyl -pyrrolidin-1-yl)-methanone,
[2,6-Difluoro-4-(pyridin-2-ylmethoxy)-phenyl]-(2-(S)-pyrrolidin-1-ylmethyl -pyrrolidin-1-yl)-methanone,
[2-Fluoro-4-(pyridin-2-ylmethoxy)-phenyl]-[2-(S)-(2-(R)-methyl-pyrrolidin-1 -ylmethyl)-pyrrolidin-1-yl]-methanone,
[4-(Pyrazin-2-ylmethoxy)-phenyl]-(2-(S)-pyrrolidin-1-ylmethyl-pyrrolidin-1-yl) -methanone,
4-[4-(2-(S)-Pyrrolidin-1-ylmethyl-pyrrolidine-1-carbonyl)-phenoxymethyl]-benzoic acid,
[2,6-Difluoro-4-(pyridin-2-ylmethoxy)-phenyl]-[2-(S)-(2-R)-methyl-pyrrolidin-1 -ylmethyl)-pyrrolidin-1-yl]-methanone,
[2-(S)-(2-(R)-Methyl-pyrrolidin-1-ylmethyl)-pyrrolidin-1-yl]-[4-(pyridin-2 -ylmethoxy)-phenyl]-methanone,
[4-(Pyridin-2-ylmethoxy)-phenyl]-(2-(R)-pyrrolidin-1-ylmethyl-yrrolidin-1-yl) -methanone,
[2-Fluoro-4-(6-methyl-pyridin-2-ylmethoxy)-phenyl]-[2-(S)-(2-(R)-methyl -pyrrolidin-1-ylmethyl)-pyrrolidin-1-yl]-methanone,
[4-(6-Methyl-pyridin-2-ylmethoxy)-phenyl]-[2-(S)-(2-(R)-methyl-pyrrolidin-1 -ylmethyl)-pyrrolidin-1-yl]-methanone,
[2-Fluoro-4-(4-methanesulfonyl-benzyloxy)-phenyl]-[2-(S)-(2-(R)-methyl -pyrrolidin-1-ylmethyl)-pyrrolidin-1-yl]-methanone,
[2-Fluoro-4-(4-fluoro-benzyloxy)-phenyl]-[2-(S)-(2-(R)-methyl-pyrrolidin-1 -ylmethyl)-pyrrolidin-1-yl]-methanone,
[4-(2-Benzenesulfonyhnethyl-benzyloxy)-2-fluoro-phenyl]-[2-(S)-(2-(R)-methyl -pyrrolidin-1-ylmethyl)-pyrrolidin-1-yl]-methanone,
[2-Fluoro-4-(6-methoxy-pyridin-3-ylmethoxy)-phenyl]-[2-(S)-(2-(R)-methyl -pyrrolidin-1-ylmethyl)-pyrrolidin-1-yl]-methanone, and
[4-(2-Fluoro-4-trifluoromethanesulfonyl-benzyloxy)-phenyl]-[2-(S)-(2-(R)-methyl -pyrrolidin-1-ylmethyl)-pyrrolidin-1-yl]-methanone,
or a pharmaceutically acceptable salt thereof.

12. A pharmaceutical composition which comprises a compound or salt of claim 1 and a pharmaceutically acceptable carrier.

13. A compound of formula I, or a salt thereof, as claimed in claim 1, for use in treating obesity.

\* \* \* \* \*